United States Patent
Eigler et al.

(10) Patent No.: US 7,862,513 B2
(45) Date of Patent: Jan. 4, 2011

(54) APPARATUS FOR MINIMALLY INVASIVE CALIBRATION OF IMPLANTED PRESSURE TRANSDUCERS

(75) Inventors: Neal Eigler, Pacific Palisades, CA (US); James Whiting, Los Angeles, CA (US); Brian Mann, Beverly Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 673 days.

(21) Appl. No.: 10/438,300

(22) Filed: May 13, 2003

(65) Prior Publication Data

US 2004/0019285 A1    Jan. 29, 2004

Related U.S. Application Data

(60) Provisional application No. 60/378,166, filed on May 14, 2002.

(51) Int. Cl.
*A61B 5/00* (2006.01)
*A61B 5/02* (2006.01)
*A61B 5/08* (2006.01)

(52) U.S. Cl. .................. 600/486; 600/300; 600/485; 600/561

(58) Field of Classification Search ............. 600/485, 600/529
See application file for complete search history.

(56) References Cited

U.S. PATENT DOCUMENTS

| | | | |
|---|---|---|---|
| 3,542,019 A * | 11/1970 | Gittins | 128/855 |
| 3,672,352 A | 6/1972 | Summers | |
| 3,776,221 A | 12/1973 | McIntyre | |
| 4,026,276 A * | 5/1977 | Chubbuck | 600/407 |
| 4,206,761 A | 6/1980 | Cosman | |
| 4,676,255 A | 6/1987 | Cosman | |
| 4,846,191 A * | 7/1989 | Brockway et al. | 600/561 |
| 4,850,371 A * | 7/1989 | Broadhurst et al. | 600/532 |
| 4,886,070 A | 12/1989 | Demarest | |
| 4,928,701 A * | 5/1990 | Harada et al. | 600/490 |
| 5,113,869 A | 5/1992 | Nappholz et al. | |
| 5,158,529 A | 10/1992 | Kanai | |

(Continued)

FOREIGN PATENT DOCUMENTS

WO    WO 01/87148    11/2001

(Continued)

OTHER PUBLICATIONS

Gorlin, Richard et al., "The Valsalva maneuver as a test of cardiac function: pathology, physiology and clinical significance." American Journal of Medicine 22: Feb. 1957. pp. 197-212.

(Continued)

*Primary Examiner*—Patricia C Mallari
(74) *Attorney, Agent, or Firm*—Knobbe, Martens, Olson & Bear, LLP

(57) ABSTRACT

This invention relates generally to apparatus and methods for the calibration of implanted pressure transducers. It is an object of several embodiments of the present invention to provide apparatus and methods for the calibration of one or more implanted pressure transducers implanted in the body of medical patients. Various embodiments of the present invention are particularly advantageous because they offer a calibration system that is less invasive than the systems currently available.

75 Claims, 11 Drawing Sheets

U.S. PATENT DOCUMENTS

| | | | |
|---|---|---|---|
| 5,290,231 A | 3/1994 | Marcadis et al. | |
| 5,299,119 A | 3/1994 | Kraf et al. | |
| 5,324,327 A | 6/1994 | Cohen | |
| 5,437,284 A | 8/1995 | Trimble | |
| 5,477,860 A | 12/1995 | Essen-Moller | |
| 5,485,848 A * | 1/1996 | Jackson et al. | 600/485 |
| 5,533,511 A * | 7/1996 | Kaspari et al. | 600/485 |
| 5,535,738 A * | 7/1996 | Estes et al. | 128/204.23 |
| 5,566,680 A * | 10/1996 | Urion et al. | 600/561 |
| 5,582,179 A * | 12/1996 | Shimizu et al. | 600/500 |
| 5,590,649 A | 1/1997 | Caro et al. | |
| 5,617,873 A | 4/1997 | Yost et al. | |
| 5,693,075 A | 12/1997 | Plicchi et al. | |
| 5,697,375 A * | 12/1997 | Hickey | 600/486 |
| 5,713,371 A | 2/1998 | Sherman et al. | |
| 5,749,909 A | 5/1998 | Schroeppel et al. | |
| 5,788,642 A | 8/1998 | Hamatake et al. | |
| 5,810,734 A | 9/1998 | Caro et al. | |
| 5,830,131 A | 11/1998 | Caro et al. | |
| 5,833,618 A | 11/1998 | Caro et al. | |
| 5,868,135 A * | 2/1999 | Kaufman et al. | 600/300 |
| 5,968,010 A | 10/1999 | Waxman et al. | |
| 6,017,313 A * | 1/2000 | Bratteli et al. | 600/485 |
| 6,024,704 A * | 2/2000 | Meador et al. | 600/486 |
| 6,045,509 A | 4/2000 | Caro et al. | |
| 6,120,442 A | 9/2000 | Hickey | |
| 6,126,611 A * | 10/2000 | Bourgeois et al. | 600/529 |
| 6,210,346 B1 | 4/2001 | Hall et al. | |
| 6,234,973 B1 | 5/2001 | Meador et al. | |
| 6,248,083 B1 * | 6/2001 | Smith et al. | 600/585 |
| 6,292,697 B1 | 9/2001 | Roberts | |
| 6,299,583 B1 | 10/2001 | Eggers et al. | |
| 6,322,514 B1 * | 11/2001 | Holte | 600/481 |
| 6,328,699 B1 | 12/2001 | Eigler et al. | |
| 6,332,869 B1 * | 12/2001 | Ogura et al. | 600/490 |
| 6,338,718 B1 | 1/2002 | Ogura | |
| 6,364,834 B1 | 4/2002 | Reuss et al. | |
| 6,371,921 B1 * | 4/2002 | Caro et al. | 600/485 |
| 6,383,142 B1 | 5/2002 | Gavriely | |
| 6,475,153 B1 * | 11/2002 | Khair et al. | 600/485 |
| 6,491,639 B1 * | 12/2002 | Turcott | 600/508 |
| 6,494,830 B1 * | 12/2002 | Wessel | 600/300 |
| 6,501,983 B1 | 12/2002 | Natarajan et al. | |
| 6,553,263 B1 | 4/2003 | Meadows et al. | |
| 6,650,939 B2 | 11/2003 | Taepke et al. | |
| 6,669,632 B2 * | 12/2003 | Nanba et al. | 600/300 |
| 6,760,628 B2 | 7/2004 | Weiner et al. | |
| 7,018,341 B2 * | 3/2006 | Wright et al. | 600/538 |
| 7,195,594 B2 | 3/2007 | Eigler et al. | |
| 2001/0047127 A1 * | 11/2001 | New et al. | 600/300 |
| 2002/0072647 A1 * | 6/2002 | Schock et al. | 600/18 |
| 2002/0133200 A1 | 9/2002 | Weiner et al. | |
| 2003/0195571 A1 * | 10/2003 | Burnes et al. | 607/9 |
| 2004/0111034 A1 * | 6/2004 | Lin et al. | 600/485 |

FOREIGN PATENT DOCUMENTS

| | | |
|---|---|---|
| WO | WO 02/065894 | 8/2002 |

OTHER PUBLICATIONS

"A Noninvasive Method of Predicting Pulmonary-Capillary Wedge Pressure," Kevin M. McIntyre, M.D., et al., The New England Journal of Medicine, Dec. 10, 1992, pp. 1715-1720, vol. 327, No. 24.

"The Valsalva Maneuver as a Test of Cardiac Function; Pathologic Physiology and Clinical Significance," Richard Gorlin, M.D., et al., The American Journal of Medicine, Feb. 1957, pp. 197-212, vol. 22, No. 2.

* cited by examiner

FIG. 7a. Left atrial and upper airway pressure tracings during a mechanically applied pressure perturbation in an anesthetized experimental animal (pig).
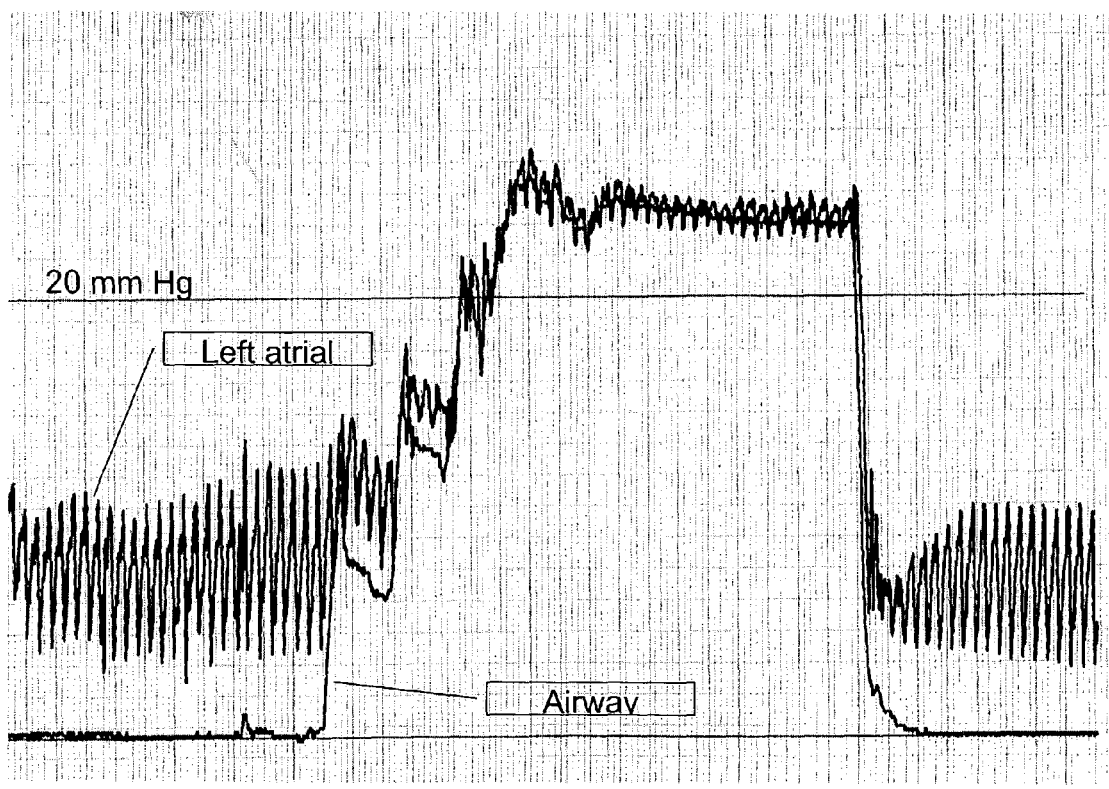

FIG. 10 Flowchart for use of the current invention to improve pressure-directed therapy

A. Pressure Calibration
    1. Calibrate pressure
    2. Date stamp ambient pressure reading
    3. Calculate valid ambient pressure range B. Pressure Measurements
    1. Measure pressure
    2. Are ambient and measured pressures within valid calibrated ranges?
        a. NO
            i. Instruct Pt to recalibrate (GO TO A)
            ii. GO TO B
        b. YES: GO TO C C. Deliver therapy

APPARATUS FOR MINIMALLY INVASIVE CALIBRATION OF IMPLANTED PRESSURE TRANSDUCERS

RELATED APPLICATIONS

The present application claims priority benefit of co-pending, provisional patent application Ser. No. 60/378,166, filed May 14, 2002, which is hereby incorporated by reference in its entirety herein. The present application is a continuation of U.S. patent application entitled METHOD FOR MINIMALLY INVASIVE CALIBRATION OF IMPLANTED PRESSURE TRANSDUCERS, Ser. No. 10/438,309, filed simultaneously herewith on May 13, 2003, now U.S. Pat. No. 7,195,594, which is incorporated by reference in its entirety herein.

BACKGROUND OF THE INVENTION

1. Field of the Invention

This invention relates generally to apparatus and methods for the calibration of implanted pressure transducers.

2. Description of the Related Art

Pressure transducers have been used to measure physiologic pressures in a variety of locations within the body including the major blood vessels, cardiac chambers, body cavities, viscera, and tissues. Pressure transducer types have included devices with differing mechanisms of action such as: piezoelectric crystals, optical, capacitance, inductance, electrolytic, and resistive strain gauge manometers. Manometer theory, invasive physiologic pressure measurement, recording, and calibration are discussed in Mackay, Nichols et al., and Milnor, all herein incorporated by reference.

The output of a pressure transducer is a signal that is related in a known way to the pressure. In some cases, the signal is electrical in nature, such as a resistance, capacitance, inductance, or voltage that changes as a function of applied pressure. In one aspect, the signal has many different forms, depending on the type of transducer. Some other examples of pressure transducer signals include, but are not limited to, change of the frequency of an oscillator in response to pressure, change in color in response to pressure, and change in position of an indicator dial in response to pressure. It will be clear to one skilled in the art that various embodiments of the present invention applies equally well to any form of pressure transducer output signal. In one aspect, the output signal of a pressure transducer is a one to one function of the applied pressure, and in general depends on other variables. This relationship can be written as:

$$s = f(P, c_0, c_2, \ldots, c_n);$$

where s is the transducer output signal, which is a function, f, of:

P, the pressure applied to the transducer; and $c_0, c_1, c_2, \ldots, c_n$, additional parameters that determine the relationship between input pressure and output signal.

To obtain a measurement of pressure from the pressure transducer signal, the inverse function of f(P), written $f^{-1}(s)$, must be known. This can be written as:

$$P' = f^{-1}(s, c_0, c_1, c_2, \ldots, c_n)$$

where P' is the measured pressure and where the inverse function also depends on the additional parameters $c_0, c_1, c_2, \ldots, c_n$.

For example, in a typical linear pressure measurement system, the system can be approximated by the expression:

$$s = a \cdot (P - P_0) = f(P, c_0, c_1),$$

where $c_0$ and $c_1$ are identified with a and $P_0$, respectively;

s is the transducer's output signal;

P is the physiologic pressure that is detected by the pressure transducer, such as a resistive strain gauge;

$P_0$ is the pressure at which the transducer output is zero, sometimes called the "baseline pressure;" and a is the "gain."

In this simple example, it is clear that the transducer signal is a linear function of pressure with a equal to the slope of the signal versus pressure plot, and $P_0$ and $-a P_0$ equal the x and y intercepts, respectively.

The inverse function is obtained by solving the output function for the pressure. In this example:

$$P' = (1/a') \cdot s + P_0'$$

where P' is the measurement of the pressure;

a' is the assumed value of the gain parameter. The quantity (1/a') is sometimes called the "scale factor" or "calibration factor;"

s is the transducer output signal; and $P_0'$ is the assumed value of the baseline pressure, also known as the "offset."

If the assumed values for the parameters, a' and $P_0'$, are equal to the true values, a and $P_0$, that determined the output of the transducer, the measured value P' will be equal to the true pressure P, and the transducer is said to be calibrated.

Thus, calibration of the transducer consists in general of determining the values of the parameters $c_0, c_1, c_2, \ldots, c_n$ of the transducer output function, in this example the two parameters a and $P_0$ (gain and offset), so that the inverse function of the transducer output signal will be equal to the true pressure. One skilled in the art will understand that although the transducer output function in this example was linear, the discussion of calibration is not limited to linear functions. However, the output signal should preferably be a one-to-one function of applied pressure, which guarantees that the inverse function exists and is also a one-to-one function, allowing the pressure to be calculated from the output signal once the transducer is calibrated. In some cases, a pressure transducer is calibrated by applying known pressures, observing the corresponding output signals, then solving the system of equations relating the known pressures and observed outputs for the unknown parameter values. In general, the minimum number of different pressure-output pairs required to solve for the parameters is equal to the number of unknown parameters. In the above example, there were two parameters, gain and offset, so at least two different pressures would need to be applied and the output signal recorded to determine both parameters.

Calibration may be performed at the time of manufacture of the transducer system. The transducer will then accurately measure true pressure as long as the true parameters determining transducer output remain constant. In reality, however, parameters such as gain and offset may change over time, a phenomenon known as "drift." Indeed, currently available transducer devices experience some degree of drift. Because of drift, transducer devices must be periodically recalibrated to ensure accurate readings.

A number of factors may contribute to this drift effect. These factors include changing atmospheric pressure, temperature, humidity, damping, material creep, fatigue, and aging of pressure transducer and electronic components. For example, the offset of a transducer incorporating a sealed chamber with an internal pressure that defines the baseline pressure will drift if the sealed chamber leaks so that its internal pressure changes. In this example, the direction of drift is determined by the initial pressure differential between the internal and external pressure. If the external pressure is lower than the internal pressure, the leak will cause an upward drift in pressure readings. If the internal pressure is lower, the leak will cause a downward drift in pressure readings. The rate of a leak is generally directly proportional to the pressure differential. In one aspect of the present invention, the rate of leak is used to maintain calibration over time.

In another example, drift due to material creep, or viscoelastic behavior, is a contributing factor in pressure transducer drift. This effect may also produce predictable calibration changes over time that depend on the intrinsic viscoelastic properties of the transducer, the pressure differential, the temperature, and even the past history of the pressure differential. In one aspect of the present invention, measured drift characteristics of a pressure transducer are utilized together with its temperature and pressure history to predict and correct for transducer drift.

As described below, various methods are known for recalibrating physiologic pressure transducers in clinical use. Each of these requires some means of access to the transducer for applying known pressures. An object of the present invention is to provide a method for recalibrating a pressure transducer that is implanted within the patient's thoracic cavity where previous methods for applying known pressure for calibration are either too invasive or do not work.

One common method to measure physiologic pressure uses a strain gauge type transducer located external to the body with a sensing membrane that is displaced by a first side being in continuity to a fluid filled catheter that communicates with the location where pressure measurement is desired. Physiologic pressure is typically measured as gauge pressure, which represents the differential of the absolute internal pressure and ambient air pressure. This is accomplished by having the second side of the sensing membrane in communication with air so that the membrane moves in response to the differential pressure. Such transducers are readily recalibrated. To do so, the first side of the membrane is temporarily exposed to air. The offset parameter is then adjusted until the pressure reading is zero. Next, the first side of the membrane is temporarily exposed to a known pressure, classically a vertical column of mercury, while the gain parameter is adjusted to match the known pressure head provided by the mercury column. Although this recalibration technique is commonly used, other physiologic pressure measuring and calibration methods are known to those skilled in the art.

To achieve higher fidelity with physiologic pressure signals, transducers have been placed in the body by mounting the transducers on or near the distal tip of a diagnostic catheter. Hamatake in U.S. Pat. No. 5,788,642 describes an apparatus for re-zeroing a catheter-based pressure transducer when it is at the in vivo measurement site in the body. This apparatus provides for a means of exposing both sides of the pressure transducer either to atmospheric pressure or to physiologic pressure to re-zero the pressure transducer.

In another approach, Demarest in U.S. Pat. No. 4,886,070 describes an apparatus for recalibrating both offset (zero) and gain of a catheter-based pressure transducer while it is at the in vivo measurement site in the body. This apparatus provides for a lumen within the catheter in communication at the distal end with the inside of the "pressure responsive element" (e.g., a diaphragm) and which is accessible at the proximal end outside the patient. In this invention, the pressure responsive element presses against the strain gauge via, e.g., a strut attached either to the diaphragm or the strain gauge, but not both. The system is manufactured so that when both the outside (measurement side) and the inside of the diaphragm are at the same pressure, the strut presses against the strain gauge, so that the strain gauge is said to be preloaded. An increase in measured pressure will further strain the gauge. The measured pressure signal is the change in resistance between the preloaded strain and the additional strain. The calibration method consists of increasing the pressure on the inside via the lumen until the indicated strain ceases to decrease, corresponding to the point at which the strut no longer presses against the strain gauge and the gauge is unloaded. One disadvantage of this approach is that it assumes that the "zero reference back pressure" (e.g., the inside pressure required to just unload the strain gauge) never drifts. This assumption does not necessarily hold, due to, for example, aging and creep in the materials and adhesives used to construct both the pressure responsive element, the coupling strut, and the strain gauge. In addition, such a device can only be used temporarily because recalibration requires access via a catheter through the patient's skin in order to manipulate the pressure inside the transducer.

Trimble, in U.S. Pat. No. 5,437,284, describes an essentially similar apparatus and method. In Trimble, however, a mechanical limit is used to establish a reference position of the pressure responsive element, instead of the point of decoupling of the pressure responsive element and the strain gauge, as taught by Demarest. As with Demarest, Trimble is based upon the possibly flawed assumption that this reference position does not itself drift and, like Demarest, Trimble requires application of a known pressure to the inside of the transducer, requiring access to the transducer through the patient's skin.

Thus, calibration issues have relegated catheter mounted pressure transducers to very limited application for patient monitoring. Indeed, use of these devices has been restricted to research studies in human patients for up to a few days or for up to several weeks in laboratory animals.

In recent years there has been a growing interest in implantable pressure transducers that can be used to diagnose and guide therapy in medical patients. Checking and maintaining calibration for such chronically implanted transducers is especially problematic because the transducer cannot easily be directly accessed to provide zeroing and reference pressures. Measuring gauge pressure requires a transducer scheme using one or two transducers. In the two-transducer scheme, the first transducer measures absolute pressure at the desired location and the second transducer, which measures absolute atmospheric pressure, is subtracted from the first. A single transducer scheme requires that a transducer has a first side of its sensing unit (diaphragm or membrane) exposed to the location of the desired pressure measurement and its second side exposed to the ambient atmosphere or its equivalent. Having direct continuity to the ambient atmosphere may not be practicable because this creates a path for the ingress of infective organisms. Several calibration methods for implanted pressure transducers have been described. Attempts have been made to use the interstitial pressure in the subcutaneous spaces as an atmospheric reference equivalent. Subcutaneous pressure, however, may differ from atmospheric pressure for a variety of reasons, especially when there are rapid changes in atmospheric pressure.

Meador, in U.S. Pat. No. 6,234,973, describes a pressure monitor for a cardiac pacemaker where a first transducer is used to measure a physiologic pressure and a second transducer is used to supply an atmospheric reference pressure. The second transducer is located superficially at or near the pacemaker generator to provide compensation for changes in atmospheric pressure. This transducer can be located subcutaneously with a subcutaneous access port that can be entered with a hypodermic needle for calibration of pressure. Such an arrangement would allow for calibration of the second subcutaneous transducer, but has the disadvantage of requiring penetration of the skin with the attendant discomfort and risk of infection. The device described in Meador has the additional limitation that the primary transducer located in the heart is not calibrated.

Cosman, in U.S. Pat. Nos. 4,676,255 and 4,206,761, describes a calibration method for an intracranial implantable pressure sensor that does not require direct access to the transducer via catheter or hypodermic needle. Rather, in vivo calibration is performed utilizing variations of positive and negative pressures applied via a chamber sealed against the skin overlying a single transducer. The sensor in this case was mounted through the skull with the inner side (first side) of the pressure responsive element exposed to the intracranial pressure and the outer side (second side) in contact with the scalp. This approach still has the disadvantage that a mechanical stop must be provided such that the differential pressure needed to drive the pressure responsive element to this reference position never changes over time. Thus, it can provide a calibration for gain, but not necessarily for offset. Despite this disadvantage, the method described does provide a means for in vivo calibration of gain (and offset if the assumption holds true) without direct access to the transducer through the skin. However, the method of using a chamber against the skin overlying the transducer would work only for those cases where access to the second side the transducer is located very superficially.

Although an implanted transducer can be calibrated just prior to implantation, even without removal from sterile packaging (as described in U.S. Pat. No. 6,292,697, incorporated by reference herein), there is no assurance that the transducer will remain calibrated. Further, once implanted, calibration cannot be easily verified without performing an invasive procedure, such as insertion of a second calibrated transducer into the body, positioned in a location where the pressure is sufficiently similar to that at the location of the permanent transducer. Such an invasive procedure may have associated risks to the health of the patient. In one study in which this was performed, Magalski et al., reported on an implanted pressure-measuring device that uses an algorithm applied to the right ventricular pressure tracing to estimate pulmonary artery diastolic pressure (PADP). PADP is a well-established surrogate for estimating the left atrial pressure (LAP), which is one of the key predictors of worsening heart failure. Initial calibrated baseline recordings in 32 patients with heart failure showed that the estimated PADP reading differed on average from the true, invasively obtained PADP by only −0.1±5.5 mm Hg. However, one year after implantation, invasive recalibration showed significant drift with an average underestimation of PADP by −3.6±6.9 mm Hg. Ultimately, transducer drift may be so significant that the measurement data become clinically useless without adequate recalibration.

Difficulty with maintaining pressure transducer calibration raises the issue of how much miscalibration is acceptable for diagnostic accuracy, especially when the results are used to make therapeutic decisions. This is important because pressure variations as small as 5 mm Hg may alter therapeutic interventions. For example, a patient with congestive heart failure will often be clinically stable and feel well (known as a condition of "compensated" heart failure) with an elevated left atrial pressure of 20 mm Hg. Such a patient may start to "decompensate," with fluid beginning to enter the lungs eventually resulting in clinical symptoms such as shortness of breath, when the left atrial pressure increases to 25 mm Hg. A patient being managed using left atrial pressure to catch the early onset of decompensation would be treated to reduce LAP, either by changing oral medications, administering drugs by injection, or even automatically delivering drugs, electrical pacing, or other therapy by an implanted device based on pressure measurements. Consequently, calibration drift errors like those reported above may be large enough to inappropriately influence medical treatment of the patient. The fact that calibration drift can profoundly affect a patient's diagnosis and ensuing therapy underscores the importance of periodic recalibration, which currently requires an invasive procedure to place a second calibrated transducer in a suitable location to assure an accurate comparison.

As discussed above, currently used methods of monitoring and maintaining calibration of implanted pressure transducers possess significant drawbacks. In various embodiments of the present invention, the calibration of implanted pressure transducers can be routinely checked and, whenever necessary, recalibrated using less-invasive methods and apparatus than those currently available. These advantages, among others, will be further understood and appreciated by reference to the written disclosure, figures, and claims herein.

SUMMARY OF THE INVENTION

It is an objective of the present invention to provide apparatus and methods for the calibration of one or more implanted pressure transducers that are implanted in the body of medical patients. Various embodiments of the present invention are particularly advantageous because they offer a calibration system that is less invasive than the systems currently available.

In one aspect of the invention, any transducer that cannot be easily accessed for direct calibration can be calibrated according to the method of the present invention. Hence, the term "implanted", as used herein, shall be given its ordinary meaning and shall include transducers that are permanently implanted and substantially permanently implanted. The term "implanted" shall also include transducers that are temporarily implanted, but which are not easily accessible to the practitioner.

In one embodiment, a method of calibrating a pressure measurement system at least partially in pressure communication with a site within a medical patient is provided. In one aspect, the method includes: measuring a first pressure at a first location, where the first location is at least partially within the medical patient; measuring a second pressure at a second location; inducing one or more perturbations, where the one or more perturbations causes the first pressure to have a calculable relationship with the second pressure; determining one or more adjustment factors based on the calculable relationship; and adjusting the pressure measurement system based at least in part on the one or more adjustment factors. In one aspect, the adjusting step occurs if the adjustment factor falls outside of a predetermined tolerance range.

These steps, and the steps recited for other embodiments described herein, need not be formed sequentially. In one embodiment, the first location is internal to the medical patient. In another aspect, the second location is internal to the medical patient, or accessible from outside the medical patient.

In one aspect of the present invention the step of adjusting the pressure measurement system includes adjusting a processor. In one embodiment, the step of adjusting a processor includes storing a value based on the adjustment factor in a memory of the processor, or altering one or more algorithms in the processor based upon the adjustment factor.

Alternatively, in another aspect, the step of adjusting said processor comprises adjusting one or more parameters, wherein the one or more parameters relates a raw pressure transducer signal to a measured pressure based upon the adjustment factor. In addition, in one aspect, the step of adjusting the processor includes adjusting a processor located within the patient, or external to the patient.

In one embodiment, the method of calibrating a pressure measurement system includes measuring a first pressure where the first pressure is indicative of a left atrial pressure, a pulmonary venous pressure, a pulmonary capillary wedge pressure, a pulmonary artery pressure, or a left ventricular pressure. In another aspect, the first pressure is indicative of a right atrial pressure, a right ventricular pressure, a central venous pressure, a systemic venous pressure, or an arterial pressure.

In one embodiment, the first location is in the thoracic cavity, within any structure contained within the thoracic cavity, within any structure of the heart, or within any cavity of the heart. In one aspect, the first location is the left atrium, the right atrium, the left ventricle, the right ventricle, or a pulmonary vein. In another aspect, the first location is a pulmonary artery, the coronary sinus, the superior vena cava, the thoracic portion of a subclavian vein, the jugular vein, intrathoracic portion of the inferior vena cava, or the intrathoracic portion of any vein. In one aspect, the first location is the aorta, an intrathoracic portion of a systemic artery, an intrathoracic portion of a blood vessel, the pleural space, the pericardial space, or the esophagus. In one aspect, the first location is the pulmonary parenchyma, the pulmonary airspaces, the upper airway of the nasopharynx, or the intrathoracic portion of a lymphatic duct. In another aspect first location is selected from the group consisting of one or more sites within one or more of the following regions: cranial cavity, ocular cavity, abdominal cavity, sinus cavity, subcutaneous tissue, hollow viscus or duct, parenchyma, pancreatic duct, bile duct, gallbladder, urinary system, and joint spaces. In one embodiment, the first location is a site within the medical patient that can be modulated by a pressure perturbation. In another aspect, the site is selected from the group consisting of one or more of the following: a body structure, an organ and a compartment.

In one embodiment of the present invention, the second location is inside the mouth, inside a body orifice, inside a mouthpiece, external to the medical patient, the air passageway of the upper respiratory system, or the air passageway of the lower respiratory system. In another embodiment, the second location is in the thoracic cavity, within any structure contained within the thoracic cavity, within any structure of the heart, within any cavity of the heart, the left atrium, the right atrium, the left ventricle, the right ventricle, a pulmonary vein, a pulmonary artery, or the coronary sinus. In another aspect, the second location is the superior vena cava, the thoracic portion of a subclavian vein, the thoracic portion of a jugular vein, the intrathoracic portion of the inferior vena cava, or the intrathoracic portion of any vein. In one aspect, the second location is the aorta, an intrathoracic portion of a systemic artery, an intrathoracic portion of a blood vessel, the pleural space, the pericardial space, the esophagus, the pulmonary parenchyma, the pulmonary airspaces, the upper airway of the nasopharynx, the trachea, or the major bronchus.

In one embodiment, the step of measuring the first pressure includes using at least one pressure transducer to measure a gauge pressure. In another embodiment, the step of measuring the first pressure includes using at least one pressure transducer to measure an absolute pressure, or a pressure relative to an arbitrary reference pressure.

In one embodiment, the step of inducing a perturbation includes performing a Valsalva maneuver.

In one aspect, the step of calibrating the pressure measurement system includes calibrating at least one pressure transducer. In one aspect, the step of calibrating is performed at different levels of perturbation, at different ambient pressures, or at different external pressures.

In another aspect of the present invention, the method of calibrating a pressure measurement system also includes providing instructions to the patient. In one aspect, the step of providing instructions to the patient includes providing instructions to the patient wherein the instructions are altered based on an ambient pressure range over which a calibration has been performed. In another aspect, the method of calibrating the pressure measurement system further includes providing instructions to a practitioner.

In another aspect, the method of calibrating the pressure measurement system further includes signaling the patient with a signaling device. In one aspect, the signaling device comprises a signal selected from the group consisting of one or more of the following: an instruction, a beep, a buzzer, a shock, a vibration, a flash, and a stimulus indicative of an instruction. In another embodiment, the signaling device comprises a personal digital assistant, or a graphical user interface. In one aspect, the signaling results in alteration of a therapy, or advises the patient that calibration is required.

In another embodiment, the method of calibrating the pressure measurement system further includes retaining information pertaining to a valid calibration range, and requesting the patient to recalibrate the pressure measurement system when a current ambient pressure is outside a valid range.

In another aspect, the step of requesting is performed only if a change in therapy is indicated, and the change in therapy is based at least in part on the second pressure. In another aspect, the signaling occurs when a temperature falls outside of a range.

In another aspect, at least part of the measurement system is implanted in a patient with congestive heart failure.

In another embodiment, the method of calibrating the pressure measurement system further includes providing a therapy. In one aspect, the therapy includes a drug delivery system, a pacing system, or a defibrillator.

In one embodiment, the step of inducing causes the first pressure to equal the second pressure at one or more identifiable points in time during the perturbation, includes active performance by the patient, or includes application to a passive patient. In one aspect, the step of inducing further includes an external application combined with active cooperation by the patient. In another aspect, the step of inducing a perturbation is selected from the group consisting of one or more of the following: performing at least one Valsalva maneuver, performing a Mueller maneuver, applying positive pressure artificial ventilation, performing unassisted normal ventilation, applying assisted positive pressure artificial ventilation, performing forced rhythmic breathing, sneezing, humming, coughing, abdominal straining, applying insufflations of a body cavity, applying external mechanical pressure, applying external hydraulic pressure, applying external pneumatic pressure, applying an acceleration, applying a deceleration, applying a change in ambient air pressure, applying a change in ambient temperature, applying a change in body temperature, applying an internal mechanical pressure, applying an internal hydraulic pressure, and applying an internal pneumatic pressure.

In one aspect, the step of inducing includes performing forced rhythmic breathing where the performing forced rhythmic breathing is performed through a restricting orifice. In another aspect, the step of inducing includes performing at least one Valsalva maneuver where the at least one Valsalva maneuver is further selected from the group consisting of one or more of the following: performing multiple Valsalva maneuvers; producing a plurality of distinct values of airway pressure during a plateau phase; performing phase I of a Valsalva maneuver; and performing phase II of a Valsalva maneuver.

In one aspect, the step inducing includes performing unassisted normal ventilation where the performing unassisted normal ventilation is further selected from the group consisting of one or more of the following: performing unassisted normal ventilation with a normal tidal volume, performing unassisted normal ventilation with an exaggerated respiratory volume, and performing unassisted normal ventilation with a maximal respiratory volume.

In another aspect, the step of inducing includes applying assisted positive pressure artificial ventilation, where the applying assisted positive pressure artificial ventilation is further selected from the group consisting of one or more of the following: applying positive pressure artificial ventilation in held inspiration; applying assisted positive pressure artificial ventilation with a normal tidal volume; applying assisted positive pressure artificial ventilation with an exaggerated tidal volume; applying assisted positive pressure artificial ventilation with controlled stepping of the airway pressure; and applying assisted positive pressure artificial ventilation with concurrent application of abdominal pressure.

In another aspect, the step of inducing includes applying insufflations of a body cavity where the applying insufflations of a body cavity is further selected from the group consisting of one or more of the following: applying insufflations of a body cavity with a gas, and applying insufflations of a body cavity with a liquid.

In another aspect of the present invention, the calculable relationship is an equality, the pressures at the first and second locations are equal at a specific interval of time, or the pressures at the first and second locations are offset by a constant at a specific interval of time. In another aspect, the calculable relationship includes at least one predicted pressure at the first location, where the at least one predicted pressure is modeled by a mathematical function. In another aspect, the calculable relationship is an experimentally verified relationship, the individual patient is their own control, a heuristic algorithm, a transfer function, a statistical model, a deterministic model, a relationship of sufficient accuracy for clinical diagnosis, a relationship within 5 mm Hg of a true pressure, a relationship that differs according to a physiologic state, a relationship that differs according to whether the patient is in compensated or decompensated heart failure, or a relationship that differs according to whether the patient has received at least one medication. In one aspect, the at least one medication is a vasodilating drug. In one embodiment, the vasodilating drug is nitroglycerin, a drug that lowers cardiac filling pressures, or a drug whose action results in a more predictable calculable relationship. In one embodiment, the calculable relationship is a relationship that includes making measurements at substantially the same moment in time in the cardiac cycle, or making measurements at substantially the same moment in time in the respiratory cycle.

In one embodiment, the method of calibrating a pressure measurement system further includes the steps of generating a signal based upon the first pressure; and transmitting the signal to a receiver. In one aspect, the step of transmitting includes transmitting radio frequency inductive coupling, radio frequency communication, or digital communication, analog communication.

In one aspect, the step of transmitting the signal to a receiver includes transmitting the signal to a receiver where the receiver includes a hand-held digital communication device, a computer, a telephone, a personal digital assistant, or a monitor. In one aspect, the step of transmitting the signal to a receiver includes transmitting the signal to a receiver where the receiver includes instructions for altering a therapy based upon said signal.

In another aspect, the method of calibrating a pressure measurement system also includes the step of generating an instruction for altering a therapy based upon said signal.

In one embodiment, the method of calibrating a pressure measurement system includes a pressure measurement system that incorporates a pacemaker, or a defibrillator.

In another aspect of the present invention, a method for calibrating a pressure measurement system in pressure communication with a site inside a medical patient is provided. In one embodiment, the method includes the steps of: measuring a first pressure in a first location, where the first location is at least partially within the medical patient; measuring at least one second pressure in at least one second location within or on the medical patient with a calibrated pressure measurement system; inducing a perturbation of pressure substantially simultaneously at the first and at least one second locations such that the pressure measured at the at least one second location is predictive of a true pressure at the first location by a calculable relationship; and comparing the first pressure and a prediction of the true pressure at the first location to establish at least one calibration parameter of the pressure measuring system.

In one embodiment, the step of measuring a first pressure at a first location includes measuring the first pressure where the first pressure is indicative of a left atrial pressure. In another embodiment, the first location is in the thoracic cavity, the left atrium, or inside the mouth. In another aspect, the step of measuring a second pressure at a second location includes measuring a second pressure at a second location where the second location is in pressure communication with the upper airway. In another aspect, the second location is in the thoracic cavity, or inside the mouth.

In another aspect, the step of inducing includes inducing that causes the first pressure to equal the second pressure at one or more identifiable points in time during the perturbation. In one embodiment, the perturbation is a Valsalva maneuver, and in another embodiment, the step of calibrating is performed at different levels of perturbation.

In another embodiment, the pressure measurement system includes a first pressure transducer, where the first pressure transducer is implanted in the patient, and the medical patient has congestive heart failure. In another aspect, the step of inducing includes a calculable relationship that is an equality, or the pressures at the first and at least one second locations are equal at a specific interval of time.

In one embodiment, the method of calibrating a pressure measurement system further includes the steps of: generating a signal based upon the first pressure; and transmitting the signal to a receiver. In one aspect, the step of transmitting includes radio frequency inductive coupling. In another aspect, the step of transmitting the signal to a receiver includes a receiver that includes a hand-held digital communication device, a computer, a telephone, or a personal digital assistant.

In one aspect, the step of measuring at least one second pressure includes measuring at least one second pressure wherein the at least one second pressure is indicative of an upper airway pressure.

In another embodiment, a method of calibrating a pressure measurement system located inside of a medical patient is provided. In one aspect of the method, the method includes the steps of: measuring a first pressure at a first location, where the first location located anywhere within the thoracic cavity; measuring a second pressure at a second location that communicates with the thoracic cavity; inducing a perturbation, where the perturbation causes the first pressure to have a calculable relationship with the second pressure; and calibrating the first pressure based at least in part on the calculable relationship.

In one embodiment, the step of measuring a first pressure at a first location includes a first location that communicates with an organ situated within the thoracic cavity, or communicates with an structure situated within the thoracic cavity. In another aspect, the step of measuring a second pressure at a second location includes a second location that communicates with an organ situated within the thoracic cavity, or communicates with a structure situated within the thoracic cavity.

In another aspect of the present invention, a method for calibrating a pressure measurement system located inside of a medical patient is provided. In one aspect, the method includes: measuring a first pressure in a first location, said first location located anywhere within the thoracic cavity; measuring at least one second pressure in at least one second location that communicates with the thoracic cavity; inducing a perturbation of pressure substantially simultaneously at the first and at least one second locations such that the pressure measured at the at least one second location is predictive of a true pressure at the first location by a calculable relationship; and using a difference between the first pressure and a prediction of true pressure at the first location to establish at least one calibration parameter of the pressure measuring system.

In one embodiment, the step of measuring a first pressure in a first location includes a first location that communicates with an organ situated within the thoracic cavity, or communicates with a structure situated within the thoracic cavity. In another aspect, the step measuring at least one second pressure in a second location includes a second location that communicates with an organ situated within the thoracic cavity, or communicates with a structure situated within the thoracic cavity.

In another aspect of the present invention, a method of calibrating a pressure measurement system located at least partially inside of a medical patient is provided. In one embodiment, the method includes: measuring a first pressure at a first location, where the first location located at least partially inside the medical patient; measuring a second pressure at a second location; inducing a perturbation, where the perturbation causes the first pressure to have a calculable relationship with the second pressure; and calibrating the first pressure to the second pressure based at least in part on the calculable relationship. In one aspect, the first and second pressures are calibrated to an absolute pressure.

In one embodiment of the present invention, a method of calibrating a pressure measurement system located inside of a medical patient is provided. In one aspect, the method includes: measuring a first pressure in a first location, where the first location is located within the thoracic cavity; measuring at least one second pressure in at least one second location, where the second location is in pressure communication with the thoracic cavity; inducing a perturbation of pressure substantially simultaneously at the first and at least one second locations, where the at least one second pressure indicates a true pressure at the first location by a calculable relationship; determining a calibration difference between the first pressure and the at least one second pressure; and adjusting the pressure measurement system based at least in part on the calibration difference.

In one embodiment of the present invention, a method of monitoring the calibration of a pressure measurement system located at least partially inside of a medical patient is provided. In one aspect, the method includes: recording a first atmospheric pressure at a first time; recording a second atmospheric pressure after a sampling period; calculating the difference between the first atmospheric pressure and the second atmospheric pressure; and providing an instruction to said medical patient based upon said difference.

In one aspect, the step of providing an instruction includes an instruction to recalibrate said pressure measurement system, or to contact a medical care provider.

In another embodiment of the present invention, a method of calibrating a pressure measurement system at least partially in pressure communication with a site within a medical patient is provided. In one aspect, the method includes the steps of: measuring a first pressure at a first location, where the first location is at least partially within the medical patient; measuring a second pressure at a second location; inducing a perturbation; comparing the first pressure to the second pressure; determining an adjustment factor based on the comparison; and adjusting the pressure measurement system based at least in part on the adjustment factor. In one aspect, the adjusting step occurs if the adjustment factor falls outside of a predetermined range.

In another embodiment of the present invention, a method of calibrating a pressure measurement system at least partially in pressure communication with a site within a medical patient is provided. In one aspect, the method includes: measuring a first pressure at a first location, where the first location is at least partially within the medical patient; measuring a second pressure at a second location; inducing a first perturbation at a first level, wherein said first perturbation causes the first pressure to have a calculable relationship with the second pressure; inducing at least one second perturbation at least one second level, where the at least one second perturbation causes the first pressure to have the calculable relationship with the second pressure, and where the at least one second level is not equal to said first level; determining one or more adjustment factors based on the calculable relationship; and adjusting the pressure measurement system based at least in part on the one or more adjustment factors. In one aspect, the adjusting step occurs if the adjustment factor falls outside of a predetermined tolerance range.

In one embodiment of the present invention, a pressure measurement calibration system is provided. In one aspect, the pressure measurement calibration system includes: one or more first sensors for measuring a first measured pressure at a first location at least partially within a medical patient; one or more second sensors for measuring a second measured pressure at a second location with respect to a medical patent; and a perturbation, where the perturbation is operable to calibrate the one or more first sensors based upon the first and second measured pressures. In one embodiment, the first location is internal to the medical patient. In another embodiment, the second location is internal to the medical patient.

In one aspect, the perturbation is operable to calibrate the one or more first sensors based upon an absolute pressure, or based upon a pressure relative to a reference pressure. In another aspect, the reference pressure is the second measured pressure. In another aspect, the perturbation is operable to calibrate the one or more first sensors based upon a gauge pressure. In one aspect, the gauge pressure is the second measured pressure.

In one embodiment, the one or more second sensors includes an obstructed mouthpiece. In one aspect, the obstructed mouthpiece includes a manometer.

In another aspect, the pressure measurement calibration system further includes a display for displaying the second measured pressure, a signal conditioning apparatus, a central processing unit of a digital computer, a comparator operable to compare the first and second measured pressures during the perturbation, a calibrator operable to adjust the at least one calibration parameter, a calibrator operable to calibrate said one or more first sensors, at least one calibration parameter, or an instruction module operable to provide a patient instruction.

In one aspect, the patient instruction is to recalibrate the one or more first sensors, to recalibrate the one or more second sensors, or to contact a physician. In another aspect, the patient instruction is provided when the first measured pressure falls outside of a previously determined range, when said second measured pressure falls outside of a previously determined range, when the difference between the first and second measured pressures falls outside of a previously determined range, when a temperature falls outside of a previously determined range, or when a date falls outside of a previously determined range.

In another embodiment, the patient instruction is to initiate said perturbation, or to control the perturbation.

In yet another embodiment, the pressure measurement calibration system further includes an automatic drug delivery device, a cardiac defibrillator, a pacemaker, an oral drug management system, or a transmitter for transmitting a signal indicative of the first measured pressure to a receiver.

In one aspect, the transmitter includes a radio frequency inductive coupling. In another embodiment, the transmitter generates a radio frequency signal, a digital signal, or an analog signal. In yet another embodiment, the receiver includes a hand-held digital communication device, a computer, a telephone, a personal digital assistant, or a monitor.

In one embodiment of the present invention, a pressure measurement calibration system is provided. In one aspect, the pressure measurement calibration includes: one or more first sensors for measuring a first measured pressure at a first location at least partially within a medical patient; one or more second sensors for measuring a second measured pressure at a second location with respect to the medical patent; and a comparator to compare the first and second measured pressures.

In one aspect, the comparator comprises a digital computer.

In another embodiment of the present invention, a pressure measurement calibration system is provided. In one aspect, the pressure measurement calibration system includes: one or more first sensors for generating a first signal indicative of a first pressure at a first location at least partially within a medical patient; one or more second sensors for generating a second signal indicative of a second pressure at a second location with respect to the medical patent; and at least one perturbation, wherein the at least one perturbation is operable to calibrate the one or more first sensors based upon said first and second measured pressures.

In yet another embodiment of the present invention, a pressure measurement calibration system is provided. In one aspect, the pressure measurement system includes: one or more first sensors for measuring a first measured pressure at a first location at least partially within a medical patient; one or more second sensors for measuring a second measured pressure at a second location with respect to the medical patent; and a calibration device, wherein the calibration device is operable to compare the first and second measured pressures and adjust at least one calibration parameter.

In another embodiment, a pressure measurement calibration system is provided. In one aspect, the pressure measurement calibration system includes: one or more first sensors for measuring a first measured pressure at a first location at least partially within a medical patient; one or more second sensors for measuring a second measured pressure at a second location with respect to the medical patent; and a perturbation operable to calibrate the one or more first sensors based upon the second measured pressure.

In another embodiment of the present invention, a pressure measurement calibration system is provided. In one aspect, the pressure measurement calibration system includes: a first means for measuring a first measured pressure at a first location inside of a medical patent; a second means for measuring a second measured pressure at a second location with respect to the medical patent; and a perturbation, where the perturbation is operable to calibrate the first means based upon the first and second measured pressures.

In one aspect, the first means includes one or more sensors. In another aspect, the second means includes one or more sensors. In another aspect, the means for inducing a pressure perturbation includes one or more perturbers. In another aspect, the pressure measurement calibration system further includes means for displaying the second measured pressure to a patient, a signal conditioning apparatus, a central processing unit of a digital computer, at least one calibration parameter, at least one calibration coefficient, or an instruction module wherein said instruction module provides a patient instruction.

In one embodiment, the patient instruction is to recalibrate the first sensor, or the second sensor, or to contact a physician. In yet another aspect, the patient instruction is provided when the first measured pressure falls outside of a previously determined range, when the second measured pressure falls outside of a previously determined range, when a temperature falls outside of a previously determined range, or when a date falls outside of a previously determined range.

In another aspect, the pressure measurement calibration system further includes an automatic drug delivery device, a cardiac defibrillator, a pacemaker, an oral drug management system, or a means for transmitting a signal indicative of the first measured pressure to a means for receiving. In one aspect, the means for transmitting includes a radio frequency inductive coupling. In another aspect, the means for transmitting generates a radio frequency signal, a digital signal, or an analog signal. In another aspect, the means for receiving comprises a hand-held digital communication device, a computer, a telephone, a personal digital assistant, or a monitor.

In one embodiment of the present invention, a pressure measurement calibration system is provided. In one aspect, the pressure measurement calibration system includes: a first means for measuring a first measured pressure at a first location inside of a medical patent; a second means for measuring a second measured pressure at a second location with respect to the medical patent; and a perturbation, where the perturbation is operable to calibrate the first means with respect to the second means.

In another embodiment of the present invention a pressure measurement calibration system is provided. In one aspect, the pressure measurement calibration system includes: a first means for measuring a first measured pressure at a first location inside of a medical patent; a second means for measuring a second measured pressure at a second location with respect to the medical patent; and a perturbation, where the perturbation is operable to calibrate the first means with respect to the second measured pressure.

In yet another embodiment of the present invention, a pressure measurement calibration system is provided. In one aspect, the pressure measurement calibration system includes: a first means for measuring a first measured pressure at a first location inside of a medical patent; a second means for measuring a second measured pressure at a second location with respect to the medical patent; and a means for perturbing, where the means for perturbing is operable to calibrate the first means based upon the first and second measured pressures.

In another embodiment of the present invention, a calibration monitor for a pressure measurement system located at least partially inside of a medical patient is provided. In one aspect, the calibration monitor includes: a recorder to measure a first atmospheric pressure at a first time and a second atmospheric pressure after a sampling period; a processor to calculate the difference between the first atmospheric pressure and the second atmospheric pressure; and an instruction, provided to the medical patient based upon the difference.

In one embodiment, the instruction is to recalibrate said pressure measurement system. In another embodiment, the instruction is to contact a medical care provider.

BRIEF DESCRIPTION OF THE DRAWINGS

FIG. 7a shows a graph of left atrial and airway pressure in a mechanically ventilated anesthetized pig undergoing a stepped positive pressure inspiration with concurrent externally applied abdominal pressure.

FIG. 10 is a flowchart for the use of the current invention to improve the safety and accuracy of pressure-directed therapy.

DETAILED DESCRIPTION OF THE PREFERRED EMBODIMENT

Measurement of a First Pressure at a First Location

Figure 1:
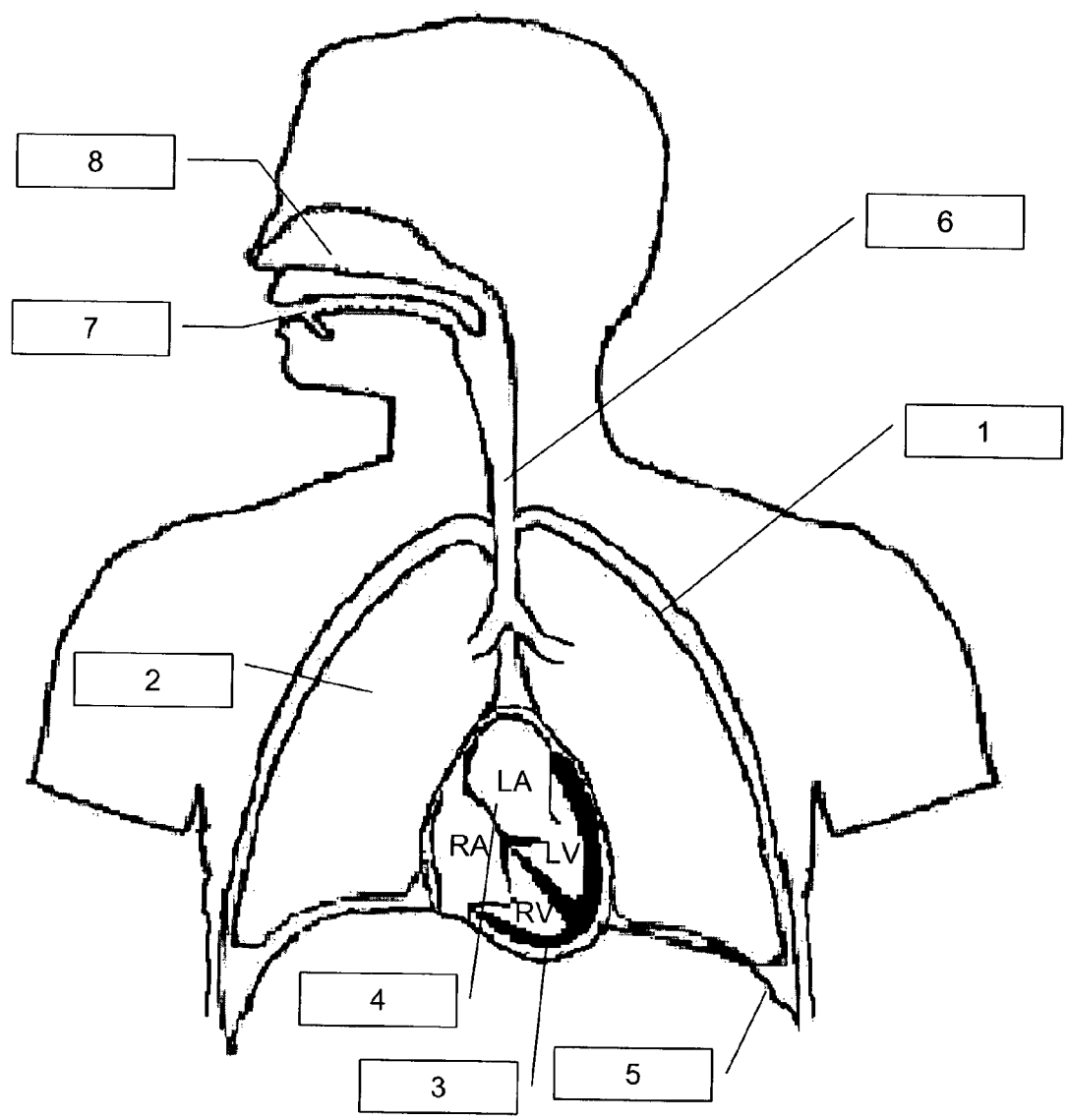
FIG. 1 is a diagram showing the thoracic cavity with heart and lungs and continuity of the lungs with the upper airway.

In one embodiment, sensor(s) are implanted to determine pressure at a first location(s) anywhere within the thoracic cavity, as shown in FIG. 1. Pressure sensors suitable for such use include, but are not limited to piezoelectric crystals, optical, capacitance, inductance, electrolytic, and resistive strain gauge manometers, and microelectromechanical systems (MEMS) devices. In one aspect, such pressure sensors are made from a variety of materials, as is well know in the art, suitable for converting a mechanical strain into an electrical signal. One example of such sensor is a silicon resistor. The sensor size is appropriate to generate a detectable signal with adequate resolution. Some sensors have a pressure sensing surface whose area ranges from a few tenths of a $mm^2$ to up to several $cm^2$.

In one embodiment, the pressure sensor has a hermetically sealed housing. In a preferred embodiment, the sensor housing consists of a titanium cylinder hermetically closed at both ends and filled with a gas. In a preferred embodiment, the cylinder has a diameter from about 1 to about 4 mm and a length of about 3 to about 15 mm. One end of the cylinder is sealed by a diaphragm that is mechanically coupled to one or more strain gauges inside the housing. In a preferred embodiment, the diaphragm is a titanium foil with a thickness of about 1 to 3 thousandths of an inch (mils). In one embodiment, strain gauges are adhered to the inside surface of the diaphragm. Strain gauges suitable for use in the one embodiment of the present invention include but are not limited to resistive strain gauges.

In a preferred embodiment, two or four resistive strain gauges are attached to the diaphragm and electrically connected to form a half or full Wheatstone bridge, respectively. The voltage across the bridge is proportional to the imbalance of strain-induced resistance between the sides of the bridge, and thereby indicates the pressure-induces strain in the diaphragm. Such technology is well known in the art. In a preferred embodiment, electronic circuitry is disposed within the housing that operates to measure the voltage across the bridge and to convert this voltage to a signal indicative of the pressure on the outside of the diaphragm. In one embodiment, the other end of the housing is sealed by a feedthrough insulator with one or more electrical conductors. In a preferred embodiment, the hermetically sealed feedthrough insulator is a ceramic material with two electrical conductors. In another preferred embodiment, the hermetically sealed feedthrough insulator has one electrical conductor.

In one embodiment, at least one sensor as described above is implanted inside of a medical patient to determine the pressure at a location anywhere within the thoracic cavity. In one aspect, such intra-thoracic locations include, but are not limited to, one or more of the following: the pleural space 1; the lungs 2; the pericardial space 3; the heart 4 including its four chambers comprising the right atrium and ventricle (RA and RV) and the left atrium and ventricle (LA and LV); the pulmonary arteries (PA) and pulmonary veins (PV); the aorta (Ao); and the superior and inferior vena cava (SVC and IVC). In some embodiments, pressure transducers can be placed in any location, including but not limited to, the blood and lymphatic vessels, the mediastinum, and the esophagus (not shown). In other embodiments, pressure transducers can be placed in a structure of the heart, or a cavity of the heart, including the left or right atrium, and the left or right ventricle. In another aspect, pressure transducers are placed in the pulmonary vein or artery, the coronary sinus, the superior vena cava, the thoracic portion of a subclavian vein, the jugular vein, the intrathoracic portion of the inferior vena cava, or the intrathoracic portion of any vein. In other embodiments, pressure transducers are placed in the aorta, the intrathoracic portion of any artery, the intrathoracic portion of any blood vessel, the pleural space, the pericardial space, the esophagus, pulmonary parenchyma, the pulmonary airspaces, the upper airway of the nasopharynx, or the intrathoracic portion of a lymphatic duct, the intrathoracic portion of any body structure, the intrathoracic portion of any device placed within the body.

Intrathoracic and nasopharangeal sites, under certain conditions, such as a Valsalva maneuver, reflect intrathoracic pressure. In some embodiments, these same intrathoracic and nasopharangeal sites are used to monitor respiratory effort, which has utility in assessing the severity of lung disease, including but not limited to asthma, chronic obstructive lung disease, and neuromuscular disorders involving the diaphragm chest wall respiratory muscles, or upper airway obstruction, such as sleep apnea.

For the purposes of illustrative example, one or more transducers are implanted by an invasive or surgical procedure for the clinical purpose of measuring pressure at first locations known to be indicative of filling of the heart with blood and that aid in diagnosing and treating illnesses such as congestive heart failure. These locations are well known to those skilled in the art, such as physicians and physiologists, and include the left ventricle, left atrium, pulmonary veins, pulmonary capillaries, the pulmonary arteries, the right ventricle, and the right atrium.

It has been appreciated for many years that, with the exclusion of certain well-known medical conditions, a key left-sided filling parameter determining the state of compensation of the left heart is the mean left atrial pressure (LAP). LAP is closely predicted by the pulmonary venous pressure (PVP), the pulmonary capillary wedge pressure (PCWP), or the pulmonary artery and left ventricular end diastolic pressures (PADP and LVEDP, respectively). Mean RA and end diastolic RV pressures can also be used to predict left sided decompensation. In addition, the RV pressure at the peak of the first derivative of pressure with respect to time during systolic contraction is sometimes used to estimate PADP.

These pressures are complex periodic time varying signals composed of the superposition of cardiac and respiratory component waves. During normal and certain pathologic conditions such as congestive heart failure, these mean or diastolic pressure indices typically vary from 0 to 40 mm Hg gauge pressure referenced to atmospheric pressure. With few exceptions, these pressure indices transiently decrease during inspiration and increase with exhalation coincident with changes in intrathoracic pressure caused by respiratory muscle contraction including the diaphragm 5 and chest wall and lung elastic recoil. These pressure indices have exaggerated increases in response to sudden perturbations in intrathoracic pressure that can result from exaggerated breathing, coughing, sneezing or straining, etc.

Induction of Perturbation

In one embodiment of the present invention, a method to induce a perturbation is provided, such that the perturbation causes the first pressure to have a calculable relationship with the second pressure. In one embodiment, this perturbation includes a voluntary, patient-initiated exaggeration of breathing known as the Valsalva maneuver, Valsalva's maneuver or simply "Valsalva." The Valsalva maneuver has been used for decades to transiently perturb cardiovascular and other physiology for diagnostic clinical purposes. The Valsalva maneuver is defined as comprising forced expiratory effort against a closed glottis and may create a transient perturbation when performed. In practice, the procedure has been standardized to consist of pinching the nostrils and having the patient blow into an obstructed mouthpiece that contains a manometer to measure upper airway 6 pressure (UAP). Patients can maintain upper airway pressure of at least 40 mm of Hg for up to 30 seconds. The Valsalva maneuver increases pressure within the thoracic cavity and thereby impedes venous return of blood to the heart. It has complex physiologic effects on heart rate, arterial blood pressure, and filling of the heart's chambers. The Valsalva maneuver is generally safe, even in ill cardiac patients, and with proper instruction can be performed correctly in most subjects. A similar state can be artificially induced by abruptly cutting off airflow egress after mechanical positive pressure ventilation and maintaining held ventilation for a similar period of time. In one aspect, this maneuver is enhanced by using, substantially simultaneously, externally or internally applied abdominal pressure to further raise intrathoracic pressure.

The Valsalva maneuver has been used clinically to terminate tachycardia (rapid heart beats), to differentiate the cause of heart murmurs, to test autonomic nervous system function, to demonstrate radiographic findings, to raise pressure in the heart, the systemic or pulmonary circulation, and in conjunction with echocardiography or arterial blood pressure measurement to detect worsening left ventricular function.

In 1957, Gorlin et al., herein incorporated by reference, reported on the pressure difference between PCWP and airway pressure, called the "effective left atrial pressure" and other hemodynamic parameters in response to Valsalva. In patients with normal or mildly elevated left-sided pressure, effective left atrial pressure decreased during straining, usually approaching zero mm Hg. Late in straining, however, there was an occasional rise in PCWP. After two seconds, "effective right atrial pressure" became equal to airway pressure, then rose after 8 seconds. In patients with more severe heart failure, characterized by a higher baseline PCWP, effective left atrial pressure had a more variable response during straining. Generally, treatment of the underlying condition was observed to normalize the response. There are other conditions that can affect the relationship of airway pressure to intracardiac pressures during Valsalva. For example, bronchospasm will lower the airway pressure relative to intrathoracic pressure. Diseases that affect the transmission of thoracic pressure to the heart such as constrictive pericarditis will prevent an appropriate cardiac response. Although these and other data discuss some of the limitations and relationships between cardiac filling pressures and airway pressure during perturbation by the Valsalva maneuver, the prior art has not appreciated that invasive intracardiac pressures can be predicted by a less-invasive assessment of airway pressure with sufficient accuracy to calibrate implanted transducers for clinical diagnostic and therapeutic purposes.

In another embodiment, inducing a perturbation comprises one or more of the following: performing a Mueller maneuver, applying positive pressure artificial ventilation, performing unassisted normal ventilation, applying assisted positive pressure artificial ventilation, performing forced rhythmic breathing, sneezing, humming, coughing, abdominal straining, applying insufflations of a body cavity, applying external mechanical pressure, applying external hydraulic pressure, applying external pneumatic pressure, applying an acceleration, applying a deceleration, applying a change in ambient air pressure, applying a change in ambient temperature. In one aspect, inducing a perturbation comprises one or more of performing multiple Valsalva maneuvers producing a plurality of distinct values of airway pressure during a plateau phase, performing phase I of a Valsalva maneuver, which generates the initial rise in intrathoracic pressure, and performing phase II of a Valsalva maneuver, also known as the plateau phase, which sustains the elevation in intrathoracic pressure.

In yet another aspect, the perturbation comprises one or more of applying unassisted normal ventilation with a normal tidal volume, applying unassisted normal ventilation with an exaggerated tidal volume (forced vital capacity), applying positive pressure artificial ventilation in held inspiration (such as sighing), applying assisted positive pressure artificial ventilation with a normal tidal volume, applying assisted positive pressure artificial ventilation with an exaggerated tidal volume, and applying assisted positive pressure artificial ventilation with controlled stepping of the airway pressure. In yet another aspect, inducing a perturbation comprises one or more of applying insufflations of a body cavity with a gas, applying insufflations of a body cavity with a liquid, and applying assisted positive pressure artificial ventilation with the addition of external or internal compression of the abdomen to increase intrathoracic pressure. For example, in one embodiment, the lungs of an intubated patient are inflated with a bag-valve mask (BVM or Ambu™), and an appropriate combination of one-way valves are used to temporarily prevent exhalation until the airway pressure reaches a predetermined threshold. Alternatively, externally applied abdominal pressure are used to achieve the same pressure rise. The pressure rise can be serially stepped to different levels, such as, for example, but not limited to, 40, 50, and 60 mm Hg. When the maneuver is completed (usually after about 10 to about 20 seconds) the patient resumes unassisted or assisted breathing, as prior to the maneuver.

Measurement of a Second Pressure at a Second Location

In a preferred embodiment of the present invention, a second, less-invasively located, calibrated transducer measuring airway pressure or some other pressure which under certain conditions is indicative of thoracic pressure, is used to determine the calibration of a first pressure transducer implanted within the thoracic cavity. In one embodiment a dual transducer system is provided to calibrate a pressure transducer located inside of a medical patient.

The PCWP, LAP, PADP, LVEDP, RA, and RVEDP vary in a highly predictable and reproducible way with upper airway pressure during the Valsalva maneuver in patients with and without congestive heart failure.

In one embodiment, patients with a history or other objective evidence of congestive heart failure are instrumented with a pulmonary artery balloon flotation catheter (Swan-Ganz®) to measure first transducer pressures RAP, RVEDP, PAD, or PCWP. In some cases, first transducer pressures are measured with a pigtail catheter placed in the left ventricle to measure LVEDP, or a trans-septal catheter is placed to measure LAP. The fluid filled catheters are connected to external calibrated resistive strain gauge transducers that measure gauge pressure.

Figure 2:
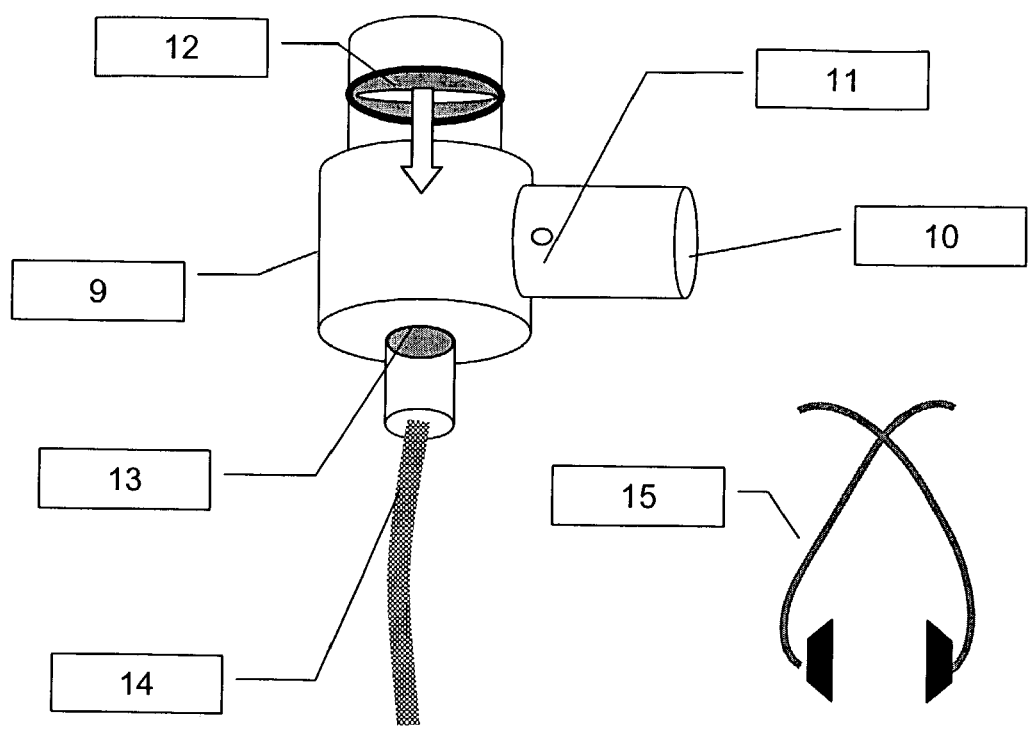
FIG. 2 shows apparatus for measuring upper airway pressure (UAP) during a Valsalva maneuver.

Patients are then instructed to perform the Valsalva maneuver and practice the maneuver several times using the apparatus schematically depicted in FIG. 2 to non-invasively measure airway pressure. A nose clip 15 is provided to prevent air escaping from the upper airway through the nasal passages 7 and 8. A mouthpiece 10 is connected to one port of a T-tube 9. It is well understood by those of skill in the art that other devices, for example, but not limited to, a breathing tube may used instead of or in addition to mouthpiece 10. A tiny air leak 11 can be created to assure that airway pressure is the result of increase intrathoracic pressure rather than a localized increase in pharyngeal pressure. A second port of the T-tube is connected to a one-way valve 12 that allows airflow during inspiration and blocks airflow during exhalation. The third port of the T-tube is connected to a second calibrated pressure transducer that measures gauge pressure. The second transducer is electronically connected to a physiologic recorder with a real-time video monitor displaying airway pressure. Thus, the patient and the instructor have visual feedback of the effectiveness of the Valsalva maneuver on airway pressure. Subjects are instructed to make a tight seal with the lips against the mouthpiece followed by partial inhalation then forceful exhalation for approximately 10 seconds. Subjects are encouraged to maintain an airway pressure above about 40 mm Hg during this period. Visual feedback of the airway pressure helps to improve compliance with the prescribed maneuver. If baseline readings of PCWP and/or LVEDP are greater than about 20 mm Hg, subjects are treated with a vasodilating drug (e.g., nitroglycerin) to lower cardiac filling pressures, thus permitting the Valsalva maneuver to create relatively higher airway pressures. Simultaneous tracings of first and second transducer pressures and the electrocardiogram are recorded and analyzed. In one embodiment, the pressure differential between the first and second transducers is analyzed during the equilibrium Phase II of the Valsalva. In another embodiment, the pressure differential during the dynamic change in pressure introduced during the initial transient Phase I of the Valsalva is analyzed.

Figure 3:
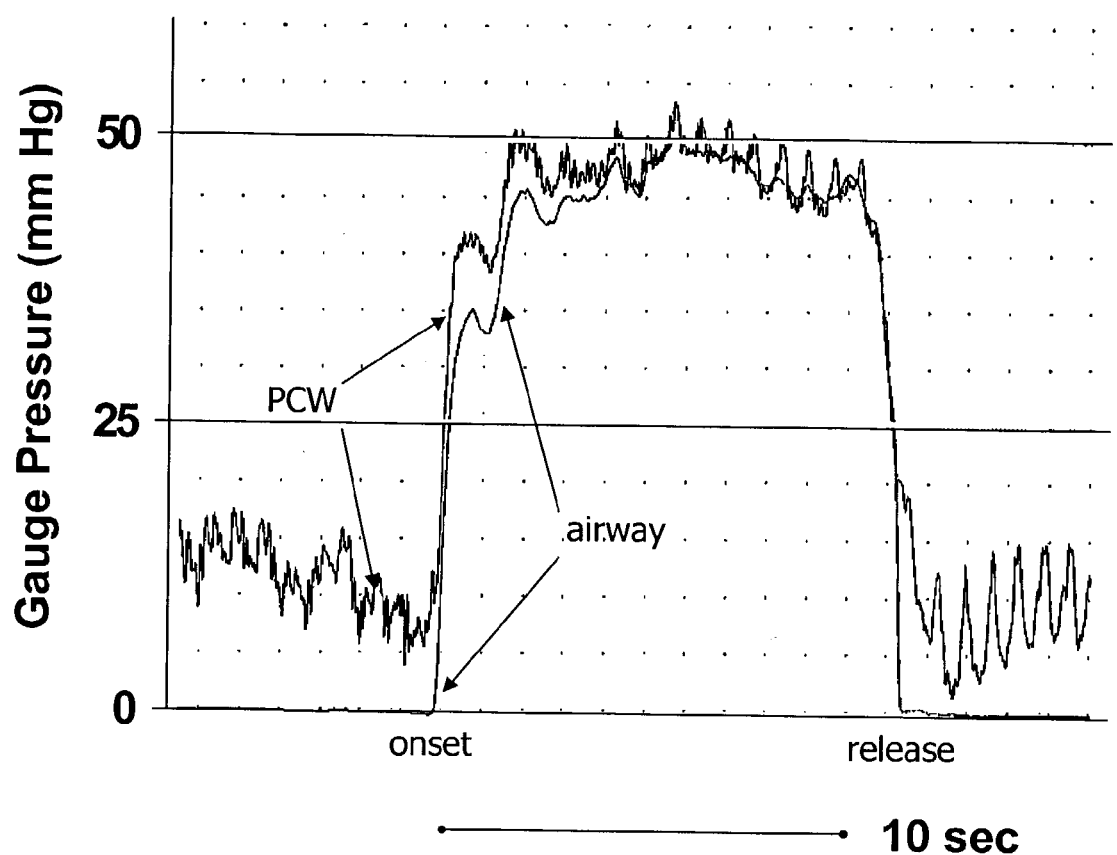
FIG. 3 shows simultaneous recordings of pulmonary capillary wedge pressure (PCWP) and UAP as a function of time before, during and after the straining portion of the Valsalva maneuver in a medical patient.
Figure 4:
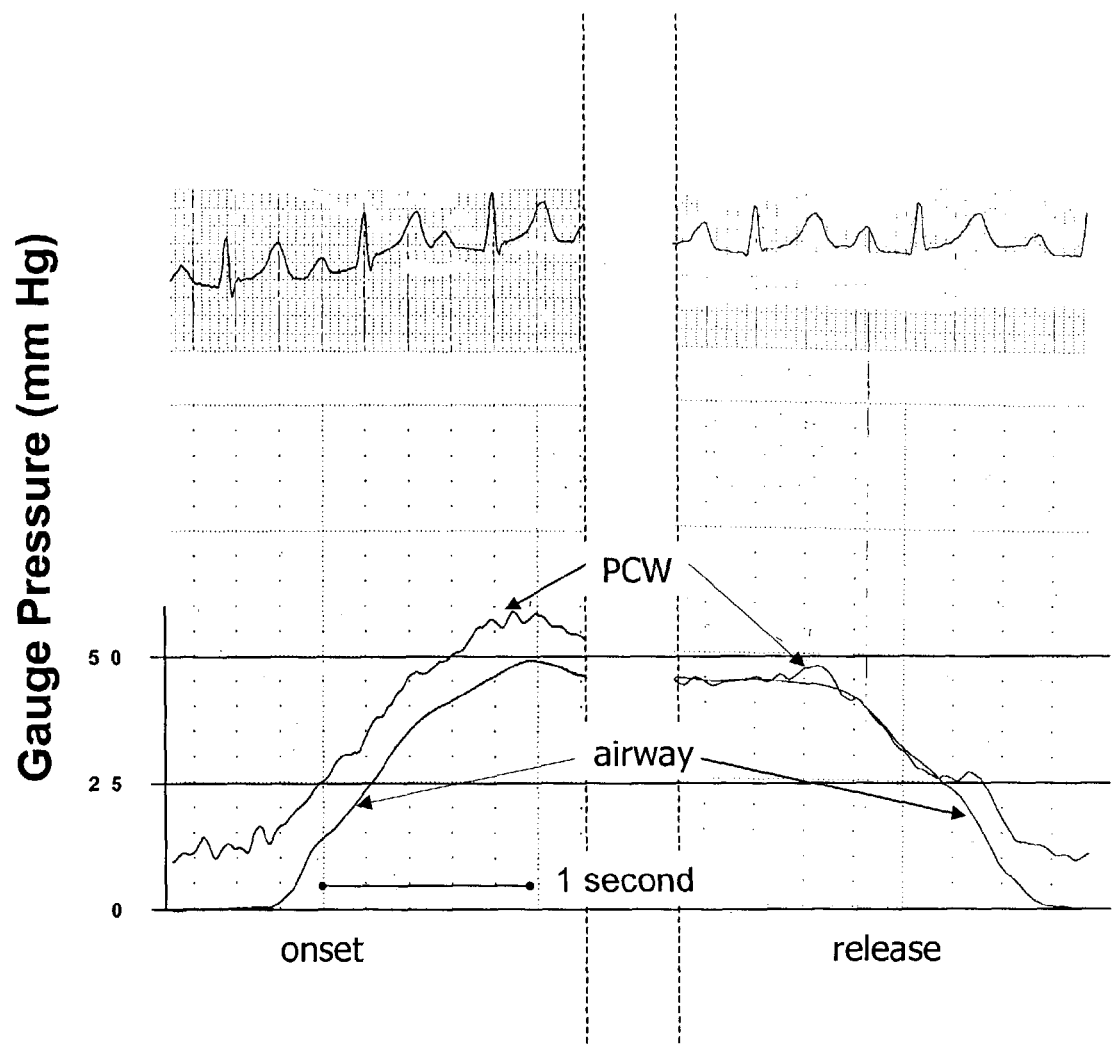
FIG. 4 shows portions of a similar recording on an expanded time scale.

FIG. 3 shows a single typical example of simultaneous recordings of upper airway pressure and PCWP as a function of time before, during and after the straining phases of the Valsalva maneuver. FIG. 4 shows portions of a similar recording on an expanded time scale. At the initiation of the Valsalva maneuver (Phase I), upper airway pressure abruptly rises, and is maintained at greater than about 40 mm Hg for more than about 10 seconds (plateau or Phase II), and then upon release of the obstruction and resumption of breathing, airway pressure falls abruptly to its baseline of zero gauge pressure (atmospheric pressure).

Prior to the Valsalva maneuver PCWP averages less than about 20 mm Hg. At the initiation of the Valsalva maneuver, PCWP increases coincidentally with rising upper airway pressure, maintaining a nearly constant differential with upper airway pressure during its initial rapid rise. Over the next three to four seconds the PCWP then declines relative to upper airway pressure remaining nearly equal to upper airway pressure during the remainder of the plateau phase. Upon release of strain and resumption of airflow, upper airway pressure and PCWP return to baseline values.

Figure 5:
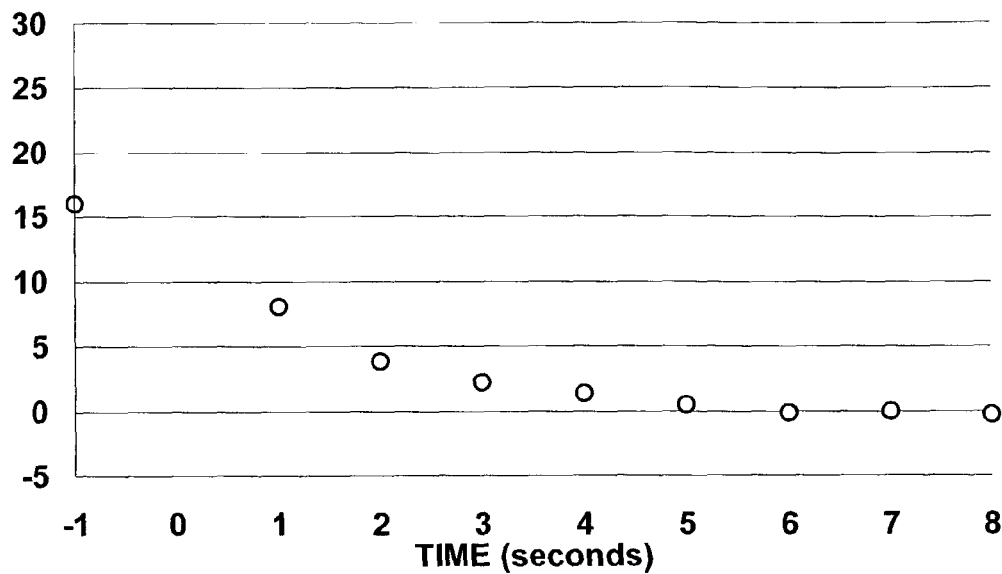
FIG. 5 shows a graph plotting the difference between PCWP and UAP as a function of time after initiation of the strain phase of the Valsalva maneuver.
Figure 5:
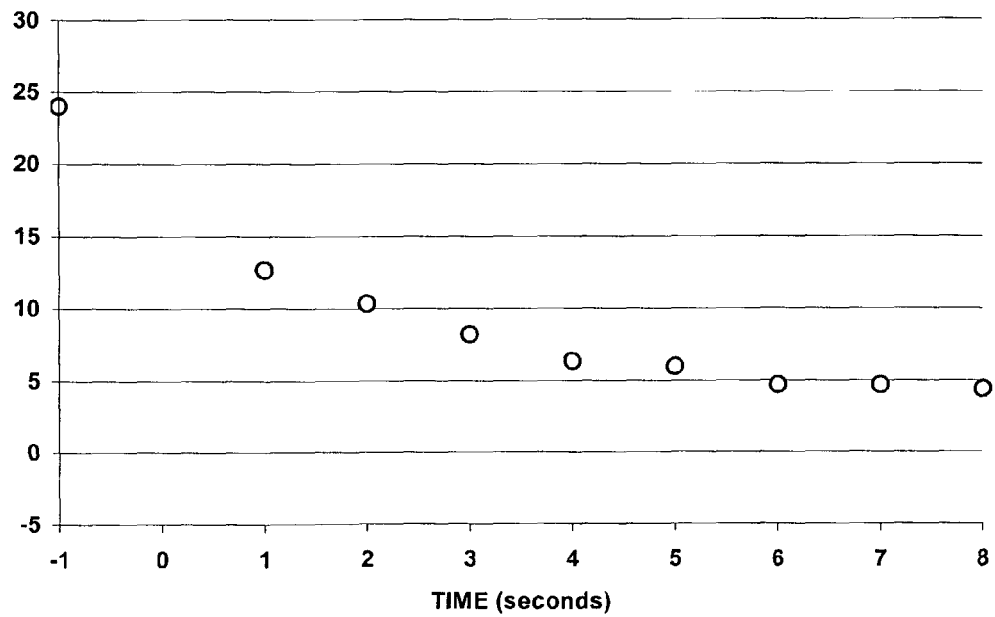
Figure 6:
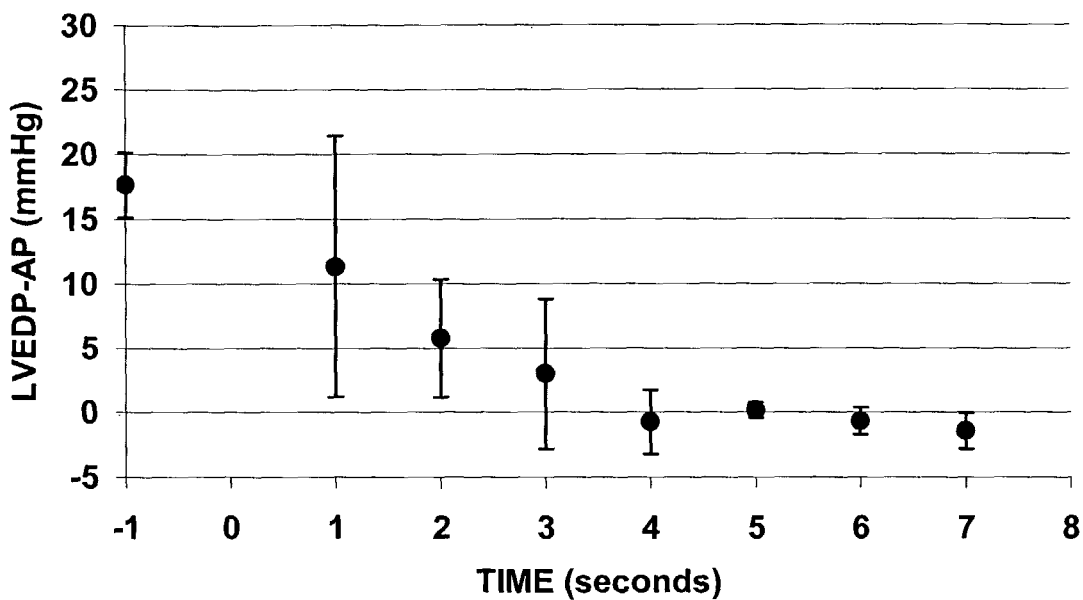
FIG. 6 shows a graph plotting the difference between of left ventricular end diastolic pressure (LVEDP) and UAP as a function of time after initiation of the strain phase of the Valsalva maneuver.
Figure 6:
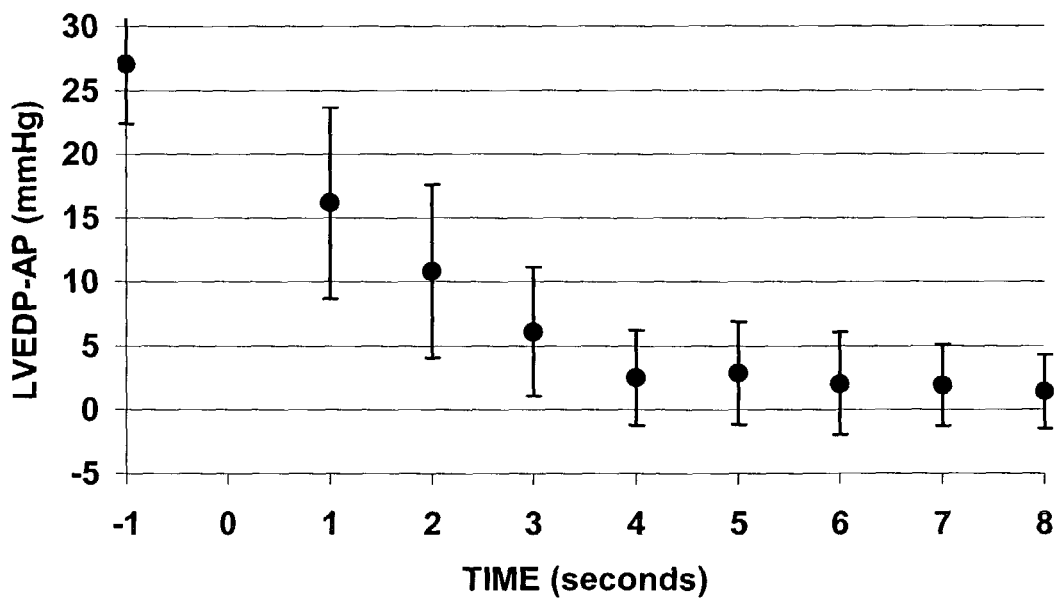

FIG. 5 shows a graph plotting the difference between PCWP and airway pressure (AP) as a function of time after initiation of the strain and release phases of the Valsalva maneuver in patients with pre-Valsalva PCWP below 20 mm Hg ("compensated" heart failure) (top) and patients with pre-PCWP values greater than 20 mm Hg ("uncompensated" heart failure) (bottom). FIG. 6 shows similar graphs for LVEDP-AP. All data are expressed as the mean±standard deviation. These data show a time-dependent relationship between first and second transducer pressures, with the two pressures approaching equivalency about four seconds into the plateau phase of the Valsalva maneuver for the patients with pre-Valsalva first pressure below 20 mm Hg. In patients with pre-Valsalva pressure above 20 mm Hg, there is a residual pressure differential even at eight seconds into the Valsalva plateau. Importantly, when these same patients are given nitroglycerin to acutely lower their pre-Valsalva PCWP or LVEDP to below 20 mm Hg, the response to Valsalva is identical to that in patients with low baseline values of PCWP or LVEDP. Similar relationships as shown in FIGS. 5 and 6 are seen when the first transducer measures RA, RVED, PAD, and LA pressures. Thus, according to one aspect of the current invention, a first pressure transducer implanted to measure pressure in any of these locations is calibrated by measuring upper airway pressure during one or more Valsalva maneuvers and making use of known relationship(s) between the pressures at these first and second locations after they have equilibrated during the plateau phase of Valsalva, as will be described below.

Figure 7:
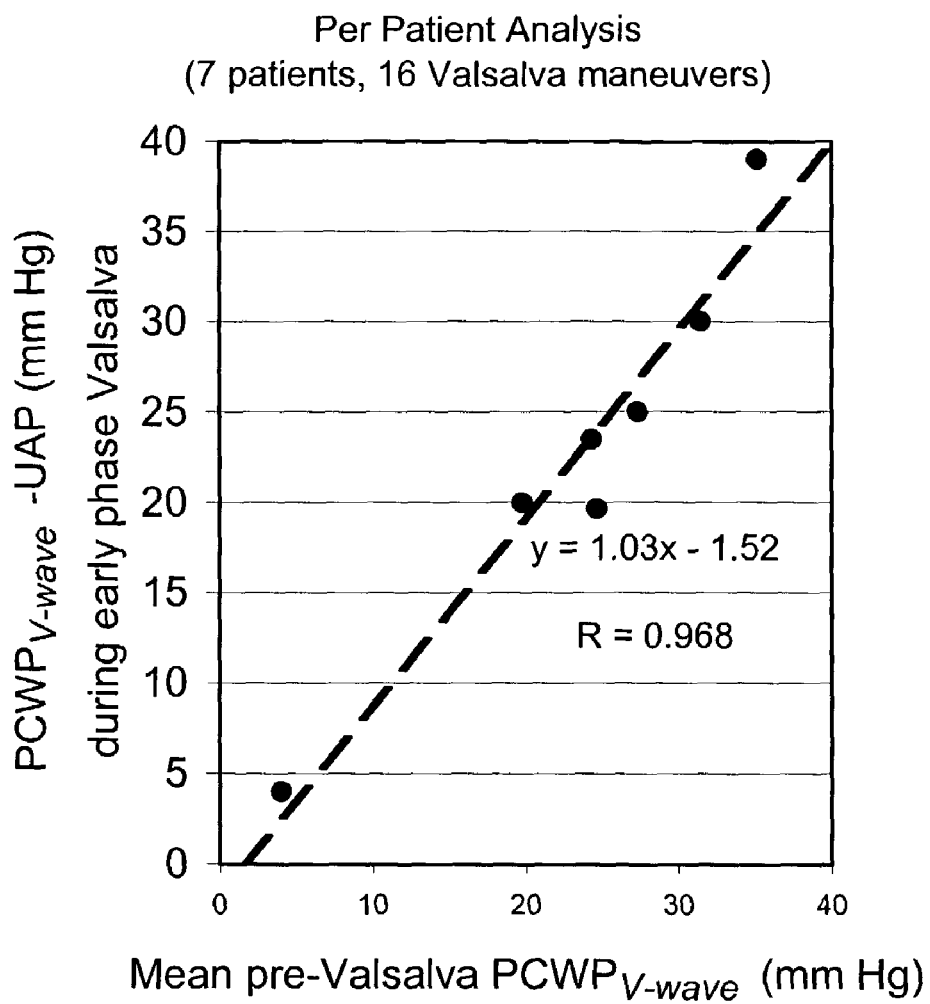
FIG. 7 shows a graph plotting the relationship between pulmonary capillary wedge pressure and upper airway pressure during the early phase of a Valsalva maneuver, demonstrating that the Valsalva can be used to transiently change intrathoracic pressure by a known amount, thus permitting the non-invasive in vivo calibration of implanted pressure transducers.

FIG. 7 illustrates the difference between PCWP and upper airway pressure during the early phase of Valsalva (e.g., phase I), just after initiation of forced expiration, in one embodiment of the present invention. In this graph, the pressure difference is plotted as a function of the corresponding pre-Valsalva PCWP in the same patient when the average UAP is zero. It is clear from this data that in one embodiment, the rise in PCWP is substantially equal to the rise in UAP early in a Valsalva maneuver. Since the UAP can be measured with an external, calibrated pressure transducer, the PCWP transducer is calibrated in vivo and non-invasively, according to another aspect of the current invention. The in vivo, non-invasive calibration of the PCWP transducer is an aspect of the present invention that is described in greater detail below.

FIG. 7a shows a graph of left atrial and airway pressure in a mechanically ventilated anesthetized pig undergoing a stepped positive pressure inspiration with concurrent externally applied abdominal pressure. This data demonstrates that Phase II Valsalva-like equilibration of UAP and LAP can be achieved by mechanical means, allowing pressure calibration to be performed according to the present invention in anesthetized subjects.

Calculable Relationships Between First and Second Pressure

In a preferred embodiment, the calibration of LAP is performed by recording the output signal of the LAP pressure transducer prior to a Valsalva maneuver, then recording both the output signal from the uncalibrated first (LAP) pressure transducer and the UAP pressure reading from a calibrated pressure gauge held in the patient's mouth during a single Valsalva maneuver. Using as an example the simple linear pressure transducer described earlier, the output signal at any given point in the cardiac cycle prior to the Valsalva can be written as:

$$s_1 = a \cdot (LAP - P_0)$$

where $s_1$ is the measured output value at a moment in time in the cardiac cycle, a and $P_0$ are the unknown gain and offset calibration parameters, and LAP is the unknown true left atrial pressure at the same moment in time in the cardiac cycle. Calibration parameter shall be given its ordinary meaning and shall include calibration coefficient as well. In the early phase of the Valsalva maneuver, immediately after the beginning of forced expiratory effort, LAP rises by the same amount as the rise in upper airway pressure, UAP, as shown in FIG. 7. Thus the pressure in the left atrium is equal to (LAP+UAP), and the output signal during the early phase of Valsalva will be:

$$s_2 = a \cdot ((LAP + UAP) - P_0)$$

where it is understood that LAP is the true LAP prior to the Valsalva, at the same point in the cardiac cycle.

As shown in FIGS. 5 and 6, about five seconds into the Valsalva maneuver the "equilibrium phase" (Phase II) of the Valsalva plateau is reached, when the PCWP, LVEDP, and LAP equilibrate with UAP because venous return is effectively blocked by the elevated intrathoracic pressure. During this late equilibrium phase the pressure in the left atrium is equal to (UAP), and the output signal from the LAP transducer becomes:

$$s_3 = a \cdot (UAP - P_0).$$

These calculable relationships are useful for calibrating a pressure sensor or transducer. The above equations for $s_1$, $s_2$, and $s_3$ may be solved for the three unknown quantities a, $P_0$, and LAP. Once the calibrated values of gain and offset have been thus determined, these values are used in the inverse function as a' and $P_0'$:

$$LAP' = (1/a') \cdot s + P_0'$$

to obtain the measured LAP pressure, LAP', from the output signal s.

In another preferred embodiment, calibration is performed using pre- and early-phase Valsalva data only. In this embodiment the output signal is recorded continuously beginning at least one cardiac cycle prior to and after initiation of the Valsalva maneuver, so that output signal values are recorded at a plurality of different rising UAP values during the early phase of Valsalva. Again referring to FIG. 7, if there are N such output signal values at N values of UAP, the N output signals will be given by the expressions:

$$s'_i = a \cdot ((LAP_i + UAP_i) - P_0); \text{ where } i=1, 2, \ldots, N.$$

The output signal values at the corresponding N matching points in the cardiac cycle prior to the Valsalva are given by:

$$s_i = a \cdot (LAP_i - P_0).$$

These calculable relationships are used to calibrate a pressure sensor or transducer. It will be clear to one skilled in the art that the above are 2N equations with N+2 unknowns (N values of LAP plus the unknown calibration parameters a and $P_0$). If N is equal to two, there are four equations which may be solved for the four unknown quantities. When N is greater than two, there are more equations than unknowns, allowing well-known statistical methods such as linear regression to be used to determine the unknowns with reduced experimental error.

In yet another preferred embodiment, the calibration of, for example, an implanted LAP transducer is performed by recording the output signal of the LAP pressure transducer and the UAP pressure reading from a calibrated pressure gauge held in the patient's mouth during two separate Valsalva maneuvers performed to produce two distinct values of UAP during the plateau phase. In one embodiment, this is done, for example, by displaying the UAP reading to the patient so that the patient can adjust his or her expiratory effort to achieve the desired UAP increase. During a first Valsalva maneuver the patient is instructed to exert a first level of expiratory effort producing a first UAP equal to $UAP_1$. The output signal from the LAP transducer during the equilibrium phase of the Valsalva plateau is given by the expression:

$$s_1 = a \cdot (UAP_1 - P_0)$$

where $UAP_1$ is the UAP as measured by the calibrated airway transducer and a and $P_0$ are the gain and offset to be determined by calibration. The patient is then instructed to perform a second Valsalva maneuver, this time at a different level of expiratory effort producing a second UAP of $UAP_2$. The output signal from the LAP transducer during the equilibrium phase of this Valsalva maneuver is given by the expression:

$$s_2 = a \cdot (UAP_2 - P_0).$$

Because $s_1$ and $s_2$, $UAP_1$ and $UAP_2$ are known, the equations for $s_1$ and $s_2$ can be solved for the two unknown calibration parameters a and $P_0$. These calculable relationships are used to calibrate a pressure sensor or transducer. As in the previously described preferred embodiment, if data is recorded for more than two different UAP levels, there will be more equations than unknowns, and statistical methods well known to those skilled in the art can be used to determine the unknown calibration parameters with reduced experimental error.

In one embodiment, the calculable relationship is a relationship in which the first and second pressures are equal or nearly equal. In another embodiment, the pressures at first and second locations are equal at a specific interval of time. In another aspect, the pressures at first and second locations are offset by a constant at a specific interval of time. In one embodiment, the predicted pressure at a first location is modeled by a mathematical function or an experimentally verified relationship. In yet another embodiment, the individual patient is his or her own control, wherein the system is recalibrated to achieve the same response seen as in the original baseline measurements for that patient. In other embodiments, heuristic algorithms, transfer functions, statistical models and deterministic models are used. In several aspects, the calculable relationship is sufficiently accurate for clinical diagnosis. In other aspects, the calculable relationship falls within 5 mm Hg of a true pressure. In some instances, the relationship differs according to a physiologic state, for example whether the patient is in compensated or decompensated heart failure or whether the patient has received any medications. In some embodiments, the calculable relationship is one that differs according to whether the medication is a vasodilating drug, including, but not limited to, nitroglycerin, a drug that lowers cardiac filling pressures, or a drug whose action results in a predictable calculable relationship. In another aspect, the calculable relationship is a relationship that comprises making measurements at substantially the same moment in time in the cardiac cycle (such as, for example, end diastole, mitral valve closure, etc.), or a relationship that comprises making measurements at substantially the same moment in time in the respiratory cycle (such as, for example, peak inspiration or end expiration).

One skilled in the art will understand that other methods of analysis can also be used in accordance with various embodiments of the current invention. Multiple algorithms can be developed that use upper airway pressure to predict LAP, PCWP, LVEDP, other cardiac pressures, or pressures at other first locations within the thoracic cavity. As described above, one type of heuristic algorithm uses the pressure change at a second calibrated transducer location during initial portion of the Valsalva strain phase to determine the pressure change at the first, uncalibrated, transducer location. In another aspect of the present invention, bounded conditions, such as the exclusion of known limitations, are used to predict the first location pressure. In one embodiment, thoracic pressure measured from the upper airway during a perturbation event, and which sufficiently exceeds the baseline physiologic pressure at the first location, is used to predict the perturbed first location pressure.

As also described above, another type of heuristic algorithm uses the late, "equilibrium" portion of the strain phase to predict pressure equivalency between the first and second transducer locations. Fitting a model function such as a decreasing exponential function to the pressure data during the strain phase, as shown in FIGS. 5 and 6, can be helpful for accurately predicting the eventual pressure equivalency. As further described above, data from multiple Valsalva maneuvers performed at different levels of strain effort can be used to obtain data sufficient to solve a system of equations for the unknown calibration parameters. Examples were given in which the transducer output was a linear function with two calibration parameters. In such case the data from the equilibrium phase of two Valsalva maneuvers is sufficient to determine the two calibration parameters. It will be obvious to one skilled in the art that additional Valsalva maneuvers could be performed to determine the additional calibration parameters of more complex transducer output functions, such as higher order polynomial functions.

It will be clear to one skilled in the art that other maneuvers can be used to manipulate intracardiac and intrathoracic pressures in a predictable way allowing non-invasive in vivo calibration of implanted pressure transducers. Other examples of maneuvers that can be used in accordance with the current invention include the Mueller maneuver, which is the forced attempted inspiration through a restricted or blocked orifice, and forced rhythmic breathing through a restricting orifice. In these examples, the intrathoracic pressure is reduced and/or increased in known relation to the reduced upper airway pressure during inspiration and/or expiration.

Calibration

More sophisticated modeling is possible using signal analysis, system theory, control theory, statistical models, etc. For example, upper airway pressure at second location(s) can be treated as a system input function in the time or frequency domains, and PCWP, PAP, etc., at the first location as an output function, again in either the time or frequency domains. If sufficiently linear, a system transfer function relating output to input during a Valsalva maneuver yields information about the model system's performance and predict what will happen with other forms of the system input function, such as forced breathing through a mouthpiece with a restrictive orifice. In one embodiment, the observed input/output relationship is used to obtain the calibration parameters for the first location (output) transducer. Additionally, it will be obvious to one skilled in the art from the above discussion that controlled stepping of the upper airway pressure (e.g., 40, 50, 60 mm Hg ... etc.) can be used to obtain and verify calibration over a broad range of pressures.

Figure 8:
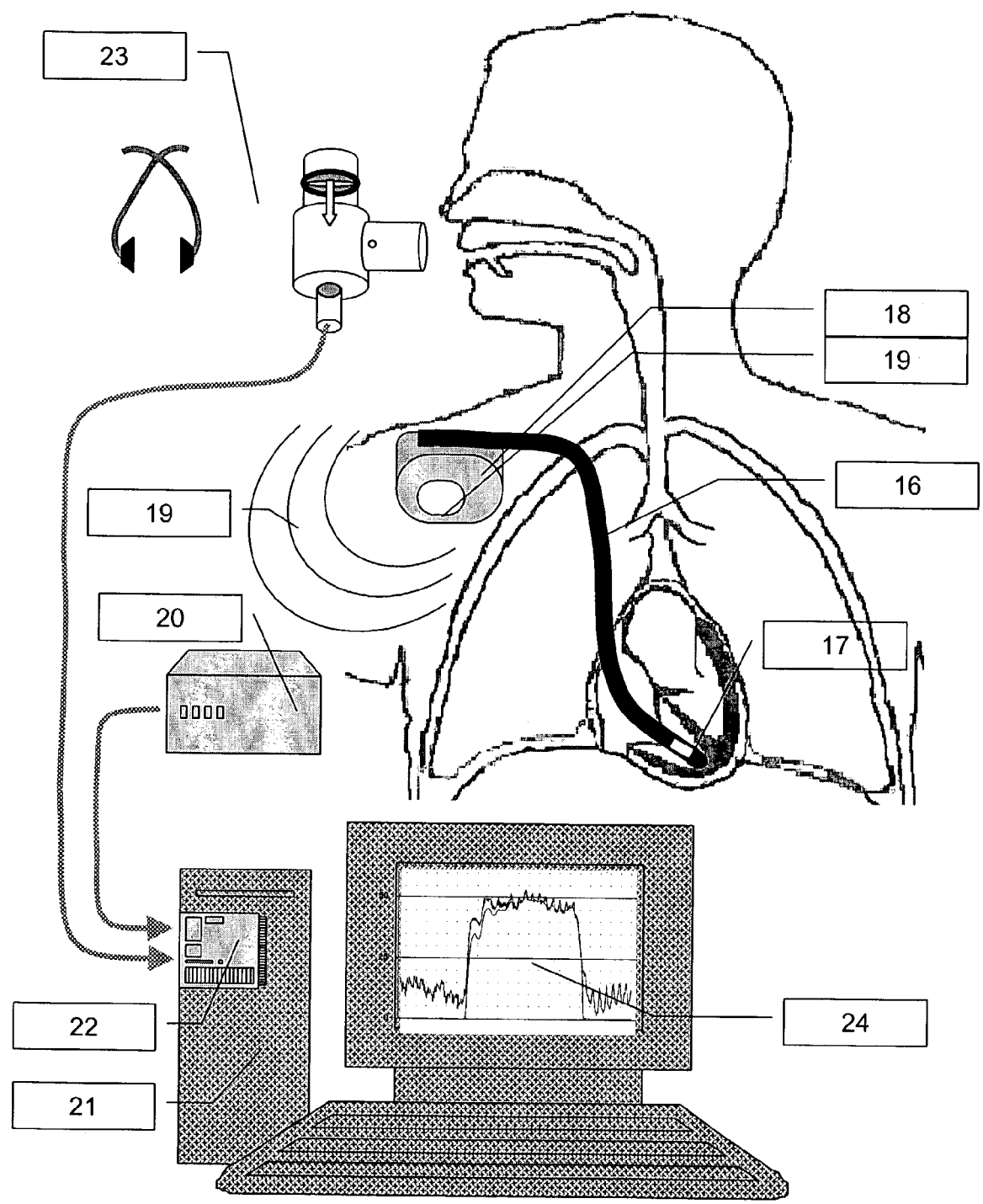
FIG. 8 is a schematic diagram of one embodiment of an apparatus suitable for the present invention.

Thus one skilled in the art can appreciate the following embodiments describing methods and apparatus for calibrating implanted pressure transducers. In FIG. 8, an implanted pressure transducer system is operated to produce a signal that, in one embodiment, is indicative of RV gauge pressure (P1) for the purpose of detecting worsening congestive heart failure. The implanted system is comprised of a pressure sensing lead 16 implanted percutaneously in a minimally invasive procedure similar to a pacemaker lead insertion. The term "minimally invasive" is to be given its ordinary meaning, as well as that the placement of a pressure transducer at a second location is less invasive, or less permanent than the transducer placed at the first location. In one embodiment the lead 16 has a distal pressure sensing membrane to detect RV pressure at a location 17, and a mechanical or hydraulic element for transmitting this pressure through the lead 16 to one side of a pressure transducer located in the system controller 18. A system controller 18 containing the necessary electronics to create a transducer output signal is connected to the lead 16 and is surgically placed in the subcutaneous tissue of the chest wall similar to a pacemaker or defibrillator generator. The controller 18 may contain power management and memory components. A second pressure-sensing membrane 19 is in contact with the subcutaneous tissue and senses the tissue pressure as a surrogate for atmospheric pressure. The second pressure-sensing membrane 19 transmits its sensed pressure via mechanical or hydraulic coupling to the other side of the pressure transducer located in the controller. With one side of the transducer in communication with the first location 17 in the RV via the lead 16 and the other side of the transducer in communication with atmospheric pressure via the a membrane 19 in contact with the patient's subcutaneous tissue, the output of this first transducer is thus the RV gauge pressure, e.g., the difference between RV and atmospheric pressures. In one embodiment, the implanted pressure sensing system also includes a pacemaker or defibrillator.

According to one aspect of the current invention, calibration is periodically checked at any suitable time or location, such as during visits to the physician's office by having the patient perform Valsalva maneuvers by exhaling into a pre-calibrated apparatus 23 containing a second transducer similar to that shown in FIG. 2, such that airway pressure exceeds 40 mm Hg for at least 8 seconds. In one aspect, the patient receives nitroglycerin or other vasodilating drugs to lower the baseline left atrial pressure as required. In one embodiment, real-time pressure data from the implant is telemetrically sent to an external receiver 20. In one aspect, the patient receives visual feedback as to the adequacy of the Valsalva maneuver by a video display 24. In one aspect, the video display 24 shows tracings similar to those illustrated in FIG. 3. First and second transducer signals are the inputs to appropriate signal conditioning and digitizing apparatus 22 and subsequently analyzed and stored by a digital computer 21, which computes the calibration parameters from the data. The new calibration parameters are then sent back to the implanted device or to an external communications device where they are used to compute the inverse of the pressure sensor output function.

The first and second transducer signals are indicative of pressures in first and second locations, respectively. In one aspect, the first and second transducer signals are used to determine an adjustment factor. In one embodiment, the adjustment factor is based upon the difference between the two transducer signals. Alternatively, the adjustment factor is based upon any calculable relationship between the pressures at the first and second locations.

In one embodiment, once an adjustment factor is determined, the pressure measurement system is calibrated. For example, if the adjustment factor indicates an offset value, an offset error, a DC offset, or drift, the adjustment factor is stored in a memory location, and combined by addition (or subtraction, or any other suitable way known to those of skill in the art) to a subsequent pressure measurement taken during clinical diagnosis. In one embodiment, by adding (or subtracting) the adjustment factor calibrated output of the pressure measurement system is achieved. In one aspect, a calibrator is used to calibrate the pressure measurement system. In one embodiment, as known to those of skill in the art, the calibrator includes the electronics, hardware, software and firmware required to calculate, store, and later apply the parameters and values used to calibrate the pressure measurement system. In one aspect, the calibrator components include, or implement various algorithms to calculate, store, and later apply the parameters and values used to calibrate the pressure measurement system. For example, in one embodiment calibration software implements an algorithm that multiplies a gain factor to a pressure signal received from a pressure measurement system, and then adds an offset value to the product. In one embodiment, a comparator is used to compare the pressures measured by the pressure measurement system. In one embodiment, the comparator is a computer, microprocessor, or an electronic circuit. The comparator can also comprise software with appropriate analog to digital circuitry. As is known to those of skill in the art, the output of such comparator may include an electrical signal, analog or digital value indicative of the differences in measured pressures. In one embodiment, the comparator includes, but is not limited to, the electronics, hardware, software and firmware required to compare such pressure measurements. Such comparators are well known to those of skill in the art.

In one embodiment, once an adjustment factor is determined, the adjustment factor is compared to a predetermined adjustment factor tolerance range. If the adjustment factor falls within the tolerance range, the calibration of the system is left unchanged. In one aspect, if the adjustment factor falls outside the tolerance range, the pressure measurement system is calibrated as described, for example, above. Preferably, the adjustment factor tolerance range is at least as wide as the error in determining the adjustment factor itself. In a further aspect, the tolerance range is specified such that changes of the adjustment factor within the tolerance range produce pressure measurement changes that are medically insignificant.

Figure 9:
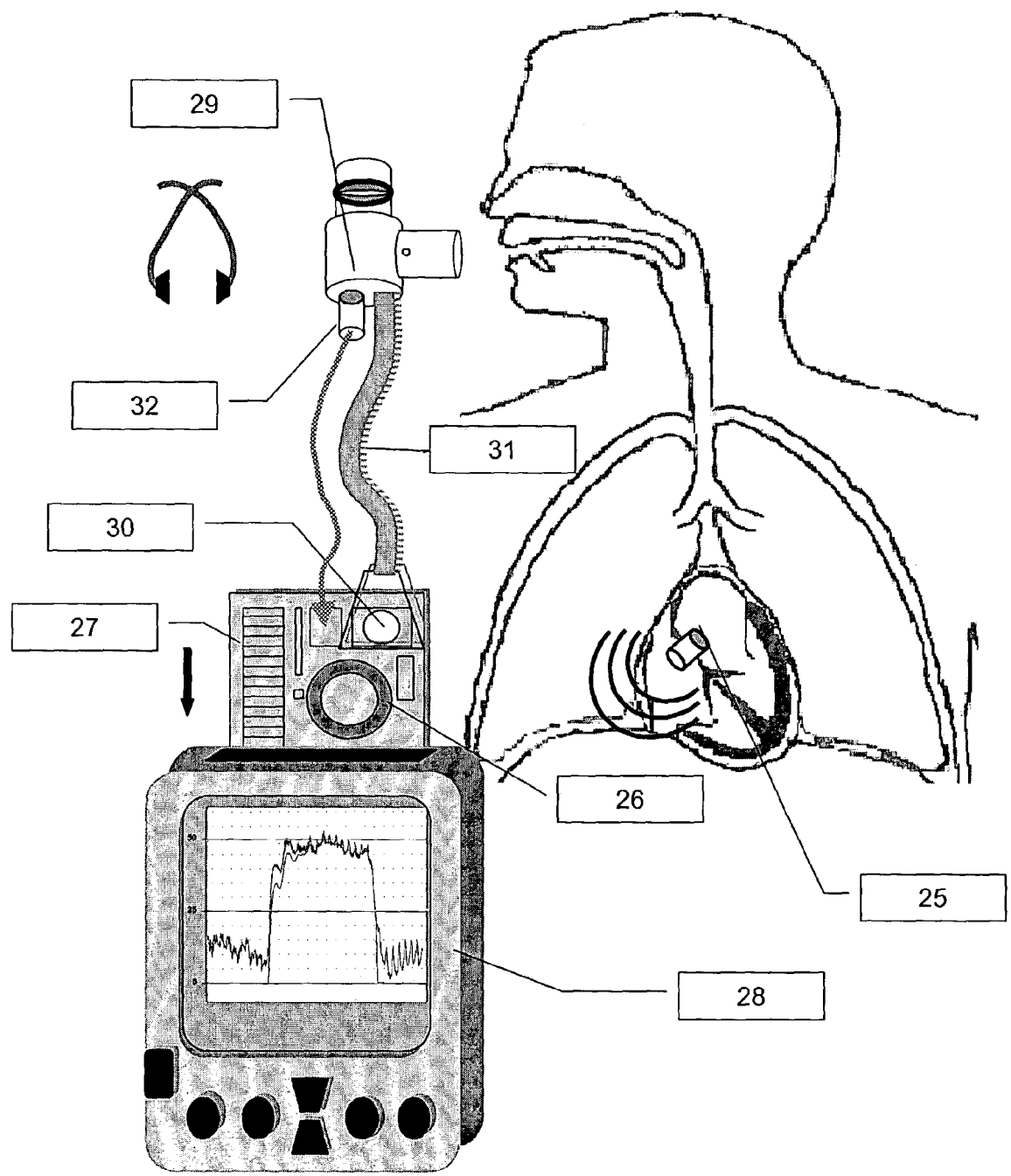
FIG. 9 is a schematic diagram of another embodiment of an apparatus suitable for the present invention.

One skilled in the art will appreciate that this method of calibration using a transient perturbation of pressure in an adjoining structure is applicable whether transducer(s) are measuring gauge pressure relative to atmospheric, or if they are referenced to some other pressure, or absolute pressure. In one aspect, the transducers are not calibrated with respect to atmospheric pressure, but are calibrated with respect to each other. For example, in one embodiment, gauge pressure can be derived by measuring the pressure difference between two transducers, each separately calibrated and referenced to absolute pressure, as depicted in FIG. 9.

In a preferred embodiment, the system to be calibrated is comprised of at least one implanted pressure sensor disposed to measure the pressure at one or more locations within the body, and at least one external pressure sensor disposed to measure the atmospheric pressure outside the body. In this embodiment, the quantities of interest are the differences between the pressures at the one or more locations within the body and the atmospheric pressure outside the body. When pressure is expressed as a difference from atmospheric pressure, the pressure is commonly referred to as a "relative pressure" or a "gauge pressure." In a preferred embodiment, both the one or more implanted sensors and the at least one external sensor are calibrated together to calibrate the gauge pressure for drift of both the implantable and external sensors. In this embodiment, neither the implanted nor external sensors need be accurately calibrated on an absolute pressure scale; it is required to calibrate only the difference between the pressure within the body and the exterior atmospheric pressure. This "relative calibration" requires less information than absolute calibration of both the implanted and external pressure sensors.

In one embodiment, two linear pressure sensors, one implanted and one external, each with unknown gain and offset, provide four parameters to be determined during calibration to obtain absolute calibration. However, if relative calibration is sufficient, it will be clear that only three parameters need be determined—the two gain parameters and the difference between the two offset parameters. Because the gauge pressure is calculated by subtracting the measured external pressure from the measured internal pressure, it is not affected by the values of the individual sensor offsets, only by the difference between the offsets.

In one aspect, an implanted pressure sensor measures pressure of the left atrium, and the invasively implanted first transducer 25 measures absolute pressure $LAP_1$ in the left atrium, such that when uncalibrated $$s_1 = a_1(LAP - B_1)$$

where LAP is the left atrial pressure, and $a_1$ and $B_1$ are the gain and offset of the first transducer, respectively. In one embodiment, the implant also contains necessary electronics to power the device and telemeter the readout of $P_1$. In one embodiment, the implant communicates with a hand-held digital communication device 28 that could be a modified personal digital assistant or cell phone.

The hand-held communications device 28 contains additional electronics 27 for digital communication with the implant. Those familiar with the art will understand that such communications with and powering of the implant could be done externally by radio frequency inductive coupling as indicated by the external coil 26. Such a system for diagnosing and treating congestive heart failure has been described in U.S. Pat. No. 6,328,699, which is incorporated by reference herein. In one embodiment, the hand-held communications device 28 contains programmed physician instructions to the patient for altering therapy based in part on the calibrated readings of the implanted first transducer 25. In another aspect, the device 28 operates by providing instructions to a practitioner, wherein the practitioner is a physician, a medical caregiver, a pharmacist, or a nurse. In another aspect, the communications includes at least one of radio frequency communication, digital communication, and analog communication.

In one aspect, to calculate left atrial pressure relative to atmospheric pressure, a second transducer 30 is used to measure absolute ambient atmospheric pressure, ATM. The signal from the second transducer 30 may be expressed as:

$$s_2 = a_2(ATM - B_2),$$

where ATM is the true atmospheric pressure, and $a_2$ and $B_2$ are the gain and offset, respectively of the second transducer 30. The measured atmospheric pressure is given by:

$$ATM' = s_2/a_2' + B_2'$$

the gauge pressure is defined as:

$$P_G = LAP - ATM$$

and the measured gauge pressure is given by $$P_G' = LAP' - ATM' = s_1/a_1' - s_2/a_2' + (B_1' - B_2').$$

It will be clear that the measured gauge pressure does not depend on the individual offsets of the two sensors, only the difference $(B_1' - B_2')$. Thus, if the two sensors are calibrated together as a pair the number of calibration parameters is reduced from four to three when measuring relative pressure.

In a preferred embodiment, calibrating both first and second transducers 25, 30 simultaneously comprises attaching the second transducer 30 to breathing apparatus 29 by sufficient caliber tubing 31 so that $P_A$ reflects airway pressure during Valsalva. In one embodiment, during the later portions of the Valsalva maneuver the left atrial pressure, LAP, becomes equal to absolute upper airway pressure, UAP. Thus, during Valsalva:

$$LAP = UAP$$

so that the true pressure difference between the two transducers locations is zero:

$$v_1/a_1' - v_2/a_2' + (B_1' - B_2') = 0$$

where $v_1$ and $v_2$ are the sensor signals $s_1$ and $s_2$, respectively, during the Valsalva.

In a preferred embodiment the gains $a_1$ and $a_2$ are known to be stable, so that only the offsets need to be periodically recalibrated due to drift. In this embodiment, a single Valsalva measurement as described here is sufficient to determine $(B_1' - B_2')$, and the calibration is complete. It will be clear to one skilled in the art that the methods described above for calibrating a pressure sensor with N calibration parameters can be applied to the implanted/exterior sensor combination described to calibrate to gauge pressure, except that only N−1 equations are required. For example, in one embodiment comprising two linear transducers, there are two gains and two offsets, for a total of N=4 parameters. Because the quantity of interest is the pressure difference rather than the two individual pressures, the number of parameters is reduced to N−1=3, as shown above. Thus, it will be clear that a series of three Valsalva maneuvers at different upper airway pressures, as described above, is sufficient to determine the gauge pressure calibration of the system if the gains also drift, and only one Valsalva maneuver is needed if only the offset parameters drift.

One skilled in the art will understand that such a calibration scheme can be utilized, with minor modification, when first and second transducers 25, 30 do not measure absolute pressure but are instead referenced to arbitrary pressures. Further, because in one embodiment first and second transducers 25, 30 do not measure gauge pressure relative to atmospheric pressure, variations are expected due to changing atmospheric conditions and changes in elevation. Atmospheric changes may vary by approximately 30 mm Hg due to changing weather conditions, and elevation changes can result in ambient pressure changes of several hundreds of mm Hg. The former would likely have only a minimal effect on calibration while the later may have a substantial effect upon calibration, particularly if gain is changing. Thus, one aspect of the present invention also includes logic so that when a change in first and second transducers 25, 30 exceeds a determined threshold, for example 30 mm Hg, the apparatus instructs the patient that there should be no change in therapy or other action taken based on first transducer 25 until after recalibration. Alternatively, if such change in altitude results in predictable drift that can be extrapolated into the future, the logic is designed to automatically adjust calibration parameters or instruct the patient regarding the frequency of re-calibration. One advantage of this embodiment is that the patient is able to recalibrate the device as often as necessary without the aid of another person or the necessity to visit the physician or hospital.

Alternative Embodiments

With respect to the two embodiments described above, other second transducer locations besides the upper airway are possible for calibrating cardiac pressures. Second transducer 30 could be an esophageal balloon pressure monitor or a transducer positioned in the vena cava or right atrium. Such locations also reflect thoracic pressure during the strain phase of the Valsalva maneuver and in some aspects are "less invasive" than the desired first transducer location. In another aspect, the second transducer can be placed in any location, including but not limited to, the air passageway of the upper or lower respiratory system, the thoracic cavity, the blood and lymphatic vessels, the mediastinum, and the esophagus. In other embodiments, pressure transducers can be placed in a structure of the heart, or a cavity of the heart, including the left or right atrium, and the left or right ventricle. In another aspect, pressure transducers are placed in the pulmonary vein or artery, the coronary sinus, the superior vena cava, the thoracic portion of a subclavian vein, the jugular vein, the intrathoracic portion of the inferior vena cava, or the intrathoracic portion of any vein. In other embodiments, pressure transducers are placed in the pleural space, the pericardial space, the esophagus, pulmonary parenchyma, the pulmonary airspaces, the upper airway of the nasopharynx, or the intrathoracic portion of a lymphatic duct. For example, if the first location is the left atrium, then a less invasive second location is transient intravenous placement of a calibrated pressure transducer in the superior or inferior vena cava, or the right atrium, all of which may be reached without crossing a heart valve or performing a septal puncture. In one aspect, during Phase II of Valsalva any deviation between the first and second transducers is ascribed to error in the first transducer.

Applications other than heart failure monitoring are also used in accordance with several embodiments of this invention. In one aspect, any site within the thoracic cavity is subject to transmitted perturbation in pressure associated with respiratory maneuvers. In one aspect, other respiratory maneuvers are determined to create transient pressure changes at locations of the first and second transducers that are related one to the other, where an empirically validated algorithm can characterize that relationship. All such maneuvers and relationships can be empirically validated before being applied as a method of transducer calibration. Other respiratory maneuvers include, but are not limited to, deep rapid breathing, breathing through a narrowed mouthpiece that restricts air flow, positive pressure ventilation, high frequency ventilation, coughing, sneezing, humming, etc. Another example is the Mueller maneuver which is the opposite of the Valsalva. In the Mueller maneuver, the patient inhales against an obstruction, creating a substantial fall in intrathoracic pressure.

In another embodiment of the current invention, first pressure transducers placed at other body locations to measure a variety of physiologic pressure parameters are calibrated in accordance with the techniques discussed herein. In another aspect, implanted pressure monitors play a role in treating other conditions, such as detecting increased intracranial pressure. In one aspect, coughing or sneezing, or Valsalva causes sudden perturbations in intracranial pressure, which relates algorithmically to the pressure changes at less invasively located second transducers. In one aspect, this relationship is sufficiently reliable as to be useful for transducer calibration. Because the present invention enables non-invasive recalibration of an implanted pressure transducer, another aspect of this invention is the use of this ability to more safely control medical devices that rely on pressure measurements for delivering therapy. FIG. 10 is a flow chart showing an aspect of this invention for improved control of pressure-based medical therapy. FIG. 10 describes the use of the invention to automatically instruct the patient to recalibrate the pressure transducers prior to delivering therapy based on pressure measurements whenever the measured ambient pressure or internal physiologic pressure falls outside a previously determined valid range. Preferred embodiments of this aspect of the invention include, but are not limited to, automatic drug delivery devices, implanted cardiac defibrillators, pacemakers, and oral drug management systems such as that described in U.S. Pat. No. 6,328,699, which is incorporated herein in its entirety by reference. In this aspect of the invention, the ambient pressure and mean first location pressure are stored in the device's memory. Each time the device measures pressure, the measured and ambient pressures are compared against the stored baseline values. If either the ambient or the internal pressure differs by more than a valid calibrated range with respect to its baseline value, the patient is instructed to perform a recalibration or to contact his physician. In another aspect of the invention, automatic notification is sent to a remote site whenever ambient or internal pressures are outside a valid calibrated range. In a further aspect of the invention, the system is programmed to suspend any pressure-based changes in therapy whenever the ambient or the internal pressures are outside a valid calibrated range until a recalibration is performed. In another aspect of this invention, the temperature at the time the external ambient pressure transducer is calibrated will be also stored in memory. If the temperature at the time of a subsequent measurement is outside the range for which the temperature compensation of the external transducer is valid, the patient will be instructed to wait until the temperature comes back into the valid range before making the measurement. In yet another aspect of the current invention, the date of each or the last recalibration is stored in memory. The patient will be directed to perform a recalibration or contact his physician before the pressure data is used to affect therapy.

Referring to FIG. 10, a pressure measurement device is calibrated at operational block 40. A date stamp and ambient pressure readings are recorded at operational block 42, and a valid ambient pressure range is then calculated at operational block 44. In operational block 46 the pressure measurement device provides a measurement of pressure. In operational block 48 the ambient pressure is compared to a valid ambient pressure range and the measured pressured is compared to a valid measured pressure range. If both values fall within their respective valid pressure ranges, the method proceeds to operational block 50, where the appropriate therapy is subsequently delivered. If either value does not fall within its respective valid pressure range, the method returns to operational block 40, whereby the pressure measurement device is calibrated once again.

While this invention has been particularly shown and described with references to preferred embodiments thereof, it will be understood by those skilled in the art that various changes in form and details may be made therein without departing from the scope of the invention.

What is claimed is:

1. A pressure measurement calibration system comprising:
   a first implantable sensor adapted to be implanted at a first location at least partially within a medical patient, wherein the first implantable sensor is configured to provide a first signal indicative of a first pressure at the first location at least partially within the medical patient;
   a pressure signal receiver for receiving the first signal from the first sensor;
   a second sensor for measuring a second pressure at a second location with respect to the medical patient and for generating a second signal indicative of said second pressure;
   a processor configured to determine an adjustment factor based on said first signal, said second signal, and a perturbation, wherein said first sensor is configured to be calibrated based upon said adjustment factor;
   a mouthpiece coupled to said second sensor; and
   a communications device configured to deliver a patient instruction to said medical patient when said first pressure falls outside of a previously determined range.

2. The system of claim 1, wherein said first sensor is further operable to be calibrated based upon an absolute pressure.

3. The system of claim 1, wherein said first sensor is further operable to be calibrated based upon a reference pressure.

4. The system of claim 3, wherein said reference pressure is the second pressure.

5. The system of claim 1, wherein said first sensor is further operable to be calibrated based upon a gauge pressure.

6. The system of claim 5, wherein said gauge pressure is the second pressure.

7. The system of claim 1, wherein said second sensor comprises a manometer.

8. The system of claim 1, further comprising a display for displaying the second pressure.

9. The system of claim 1, further comprising a signal conditioning apparatus.

10. The system of claim 1, further comprising a calibrator operable to adjust at least one calibration parameter.

11. The system of claim 1, further comprising a calibrator operable to calibrate said one or more first sensors.

12. The system of claim 1, further comprising a memory coupled to at least one of said first and second sensors, wherein said memory is configured to store at least one calibration parameter.

13. The system of claim 1, wherein said patient instruction is to perform a calibration procedure.

14. The system of claim 1, wherein said patient instruction is to recalibrate said one or more second sensors.

15. The system of claim 1, wherein said patient instruction is to contact a physician.

16. The system of claim 1, wherein said patient instruction is provided when a difference between said first pressure and said second pressure falls outside a previously determined range.

17. The system of claim 1, wherein said patient instruction is provided when a temperature falls outside of a previously determined range.

18. The system of claim 1, wherein said patient instruction is provided when a date falls outside of a previously determined range.

19. The system of claim 1, wherein said patient instruction is to initiate said perturbation.

20. The system of claim 1, wherein said patient instruction is to control said perturbation.

21. The system of claim 1, further comprising an automatic therapy delivery device.

22. The system of claim 21, wherein said automatic therapy delivery device comprises an automatic drug delivery device.

23. The system of claim 21, wherein said automatic therapy delivery device comprises a cardiac defibrillator.

24. The system of claim 21, wherein said automatic therapy delivery device comprises a pacemaker.

25. The system of claim 21, wherein said automatic therapy delivery device comprises an oral drug management system.

26. The system of claim 21, wherein said automatic therapy delivery device provides a therapy level based at least in part on said first and second pressures.

27. The system of claim 21, wherein said automatic therapy delivery device is configured to provide a therapy type based at least in part upon said first and second pressures.

28. The system of claim 1, further comprising a transmitter for transmitting the first signal indicative of the first pressure to the pressure signal receiver.

29. The system of claim 28, wherein said transmitter comprises a radio frequency inductive coupling.

30. The system of claim 28, wherein said transmitter generates a radio frequency signal.

31. The system of claim 28, wherein said transmitter generates a digital signal.

32. The system of claim 28, wherein said transmitter generates an analog signal.

33. The system of claim 28, wherein said receiver comprises a hand-held digital communication device.

34. The system of claim 28, wherein said receiver comprises a computer.

35. The system of claim 28, wherein said receiver comprises a telephone.

36. The system of claim 28, wherein said receiver comprises a personal digital assistant.

37. The system of claim 28, wherein said receiver comprises a monitor.

38. A pressure measurement calibration system comprising:
   one or more first sensors configured to generate a first signal indicative of a first pressure at a first location at least partially within a medical patient;
   one or more second sensors configured to generate a second signal indicative of an upper airway pressure at a second location with respect to the medical patient, wherein said one or more second sensors comprises a mouthpiece;
   a processor configured to calibrate said one or more first sensors in response to the first and second signals and at least one perturbation; and
   an instruction module configured to provide a patient instruction based upon said first and second signals when at least one of said first and second signals falls outside of a previously determined range.

39. A pressure measurement calibration system comprising:
   a first implantable sensor adapted to be implanted at a first location at least partially within a medical patient and configured to provide a first signal indicative of a first pressure at the first location at least partially within the medical patient;
   a communication device configured to receive the first signal from the first sensor;
   one or more second sensors configured to provide a second signal indicative of a second pressure at a second location with respect to the medical patient; and
   a processor configured to compute at least one calibration parameter based upon said first and second signals while said medical patient performs a valsalva maneuver,
   wherein the communication device comprises programmed instructions for altering therapy based on said first signal and said at least one calibration parameter.

40. A pressure measurement calibration system comprising:
   a first means for measuring a first pressure at a first location inside of a medical patient;
   a second means for measuring an upper airway pressure of the medical patient at a second location with respect to the medical patient;
   a processor, configured to calibrate said first means in response to a pressure perturbation and said first and upper airway pressures; and
   an instruction module, wherein said instruction module provides a patient instruction based upon said first and the upper airway pressures when the first pressure falls outside of a previously determined range.

41. The system of claim 40, wherein said first means comprises one or more sensors.

42. The system of claim 40, wherein said second means comprises one or more sensors.

43. The system of claim 40, further comprising a perturber configured to induce said pressure perturbation.

44. The system of claim 40, further comprising means for displaying the second pressure to a patient.

45. The system of claim 40, further comprising a signal conditioning apparatus.

46. The system of claim 40, further comprising a memory coupled to said processor, wherein said processor is configured to store at least one calibration parameter with said memory.

47. The system of claim 40, further comprising a memory coupled to said processor, wherein said processor is configured to store at least one calibration coefficient with said memory.

48. The system of claim 40, wherein said patient instruction is to recalibrate said first sensor.

49. The system of claim 40, wherein said patient instruction is to recalibrate said second sensor.

50. The system of claim 40, wherein said patient instruction is to contact a physician.

51. The system of claim 40, wherein said patient instruction is provided when said first pressure falls outside of a previously determined range.

52. The system of claim 40, wherein said patient instruction is provided when said second pressure falls outside of a previously determined range.

53. The system of claim 40, wherein said patient instruction is provided when a temperature falls outside of a previously determined range.

54. The system of claim 40, wherein said patient instruction is provided when a date falls outside of a previously determined range.

55. The system of claim 40, further comprising an automatic drug delivery device.

56. The system of claim 40, further comprising a cardiac defibrillator.

57. The system of claim 40, further comprising a pacemaker.

58. The system of claim 40, further comprising an oral drug management system.

59. The system of claim 40, further comprising a means for transmitting a signal indicative of the first pressure to a means for receiving.

60. The system of claim 59, wherein said means for transmitting comprises a radio frequency inductive coupling.

61. The system of claim 59, wherein said means for transmitting generates a radio frequency signal.

62. The system of claim 59, wherein said means for transmitting generates a digital signal.

63. The system of claim 59, wherein said means for transmitting generates an analog signal.

64. The system of claim 59, wherein said means for receiving comprises a hand-held digital communication device.

65. The system of claim 59, wherein said means for receiving comprises a computer.

66. The system of claim 59, wherein said means for receiving comprises a telephone.

67. The system of claim 59, wherein said means for receiving comprises a personal digital assistant.

68. The system of claim 59, wherein said means for receiving comprises a monitor.

69. A calibration monitor for a pressure measurement system located at least partially inside of a medical patient, comprising:
   a recorder to record a first atmospheric pressure corresponding to atmospheric pressure around a blood pressure measurement system at a first time and a second atmospheric pressure corresponding to atmospheric pressure around the blood pressure measurement system after a sampling period; and
   a processor to calculate the difference between the first atmospheric pressure and the second atmospheric pressure,
   wherein the processor is configured to provide an instruction to said medical patient to take an action based upon said difference, wherein said action is to recalibrate said pressure measurement system.

70. A calibration monitor for a pressure measurement system located at least partially inside of a medical patient, comprising:
   a recorder to record a first atmospheric pressure corresponding to atmospheric pressure around a blood pressure measurement system at a first time and a second atmospheric pressure corresponding to atmospheric pressure around the blood pressure measurement system after a sampling period; and
   a processor to calculate the difference between the first atmospheric pressure and the second atmospheric pressure,
   wherein the processor is configured to provide an instruction to said medical patient to take an action based upon said difference, wherein said action is to contact a medical care provider.

71. The pressure measurement calibration system of claim 1, further comprising a display, wherein the display is configured to provide real-time feedback corresponding to said perturbation.

72. The pressure measurement calibration system of claim 71, wherein said feedback comprises an instruction to maintain a pressure during a time interval.

73. The pressure measurement calibration system of claim 1, wherein the perturbation comprises a valsalva maneuver.

74. The pressure measurement calibration system of claim 38, wherein the perturbation comprises a valsalva maneuver.

75. The pressure measurement calibration system of claim 40, wherein the pressure perturbation is a valsalva maneuver.

* * * * *